United States Patent
Parshall et al.

(10) Patent No.: US 12,198,803 B2
(45) Date of Patent: Jan. 14, 2025

(54) TECHNIQUES FOR PROCESSING WIRELESSLY BROADCAST PACKETS FROM A MEDICAL DEVICE WITH DOSE-RELATED DATA

(71) Applicant: Eli Lilly and Company, Indianapolis, IN (US)

(72) Inventors: James Harold Parshall, Westfield, IN (US); Adam Nathaniel Wiesler, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/006,683

(22) PCT Filed: Jul. 27, 2022

(86) PCT No.: PCT/US2022/038423
§ 371 (c)(1),
(2) Date: Jan. 24, 2023

(87) PCT Pub. No.: WO2023/009566
PCT Pub. Date: Feb. 2, 2023

(65) Prior Publication Data
US 2024/0038379 A1 Feb. 1, 2024

Related U.S. Application Data

(60) Provisional application No. 63/203,762, filed on Jul. 30, 2021.

(51) Int. Cl.
*G16H 40/63* (2018.01)
*H04W 4/80* (2018.01)

(52) U.S. Cl.
CPC .............. *G16H 40/63* (2018.01); *H04W 4/80* (2018.02)

(58) Field of Classification Search
CPC ........ G16H 40/63; G16H 10/65; G16H 20/17; H04W 4/80
See application file for complete search history.

(56) References Cited

U.S. PATENT DOCUMENTS 8,734,394 B2   5/2014  Adams et al.
9,672,328 B2   6/2017  Saint et al.
(Continued)

FOREIGN PATENT DOCUMENTS

EP      3381493 A1    10/2018
WO    2019121613      6/2019
(Continued)

OTHER PUBLICATIONS

Youngsul et al., Data-Driven Knowledge-Based System for Self-Measuring Activities of Daily Living in IoT-Based Test, Jul. 15, 2020, Applied Sciences, vol. 10, Iss. 14. (Year: 2020).*
(Continued)

*Primary Examiner* — Christopher L Gilligan
(74) *Attorney, Agent, or Firm* — Arthur Shum

(57) ABSTRACT

A computing device is provided having a processor in communication with a memory configured to store machine-readable instructions. The processor can receive, from a wireless communication interface of a medication delivery device, an advertising packet comprising injection event information generated by the medication delivery device, analyze contextual data associated with the advertising packet to determine validation data, and choose, based on the validation data, between implementing any two or three of the following actions: (i) include the injection event information in a medication log, (ii) prompt a user for additional information, or (iii) ignore the advertising packet. The medication delivery device comprises (a) a reservoir configured to hold medication, (b) an actuating button for initiating an injection of the medication, and (c) a processing (Continued)

circuit in communication with the wireless communication interface.

12 Claims, 16 Drawing Sheets

(56) References Cited

U.S. PATENT DOCUMENTS

| | | | |
|---|---|---|---|
| 10,163,311 | B2 | 12/2018 | Herschkowitz et al. |
| 10,375,222 | B2 | 8/2019 | Mandapaka et al. |
| 10,398,852 | B2 | 9/2019 | Taylor et al. |
| 11,638,540 | B2* | 5/2023 | Halac ............... A61B 5/0031 600/347 |
| 2012/0053527 | A1 | 3/2012 | Cirillo et al. |
| 2014/0274031 | A1 | 9/2014 | Menendez |
| 2018/0028755 | A1 | 2/2018 | Philip et al. |
| 2018/0280624 | A1 | 10/2018 | Bitton et al. |
| 2018/0353698 | A1 | 12/2018 | Saint et al. |
| 2019/0134305 | A1 | 5/2019 | Srinivasan et al. |
| 2019/0192779 | A1 | 6/2019 | Nagar et al. |
| 2019/0279756 | A1 | 9/2019 | Edwards et al. |
| 2019/0340900 | A1 | 11/2019 | Herschkowitz et al. |
| 2021/0023308 | A1* | 1/2021 | Holm ............... G16H 20/17 |
| 2021/0093784 | A1 | 4/2021 | Adams et al. |
| 2021/0187197 | A1* | 6/2021 | Zade ............... A61M 5/1723 |
| 2021/0249113 | A1* | 8/2021 | Molesworth ....... G06F 21/6245 |
| 2022/0092960 | A1* | 3/2022 | Arumugam ............ H04W 4/80 |
| 2022/0109956 | A1* | 4/2022 | Volkerink ........... H02J 7/00032 |
| 2022/0150308 | A1* | 5/2022 | Hua ..................... H04L 67/14 |
| 2022/0249779 | A1* | 8/2022 | Hayter ................ G16H 50/20 |
| 2023/0033566 | A1* | 2/2023 | Helmer .................. A61M 5/24 |

FOREIGN PATENT DOCUMENTS

| | | |
|---|---|---|
| WO | 2020064681 | 4/2020 |
| WO | 2020176319 | 9/2020 |
| WO | 2020214981 | 10/2020 |
| WO | 2021048035 | 3/2021 |
| WO | WO-2022112215 A1 * | 6/2022 |

OTHER PUBLICATIONS

Patent Cooperation Treaty International Search Report of the International Searching Authority pertaining to International Application No. PCT/US2022/038423; International Filing Date: Jul. 27, 2022; Date of Mailing: Oct. 26, 2022.

Patent Cooperation Treaty Written Opinion of the International Searching Authority pertaining to International Application No. PCT/US2022/038423; International Filing Date: Jul. 27, 2022; Date of Mailing: Oct. 26, 2022.

Product Advertisement, *SmartPilot—Transforming YpsoMate Into a Smart Product System*, retrieved Jan. 20, 2023 from the internet at https://yds.ypsomed.com/en/injection-systems/smart-devices/smartpilot-for-ypsomate.html.

* cited by examiner

TECHNIQUES FOR PROCESSING WIRELESSLY BROADCAST PACKETS FROM A MEDICAL DEVICE WITH DOSE-RELATED DATA

BACKGROUND

Injection devices in the form of a syringe or which include a syringe are widely employed by medical professionals and patients who self-medicate. Patients suffering from a number of different diseases may frequently inject themselves with medication and a variety of devices have been developed to facilitate such self-medication. In one example, the use of an automatic injection device which includes mechanisms to perform some of the steps of the injection process renders it more convenient for a patient to self-medicate particularly by patients with limited manual dexterity. Automatic injection devices may be single use devices that are disposed after use.

Many injector pens and other medication delivery devices do not include the functionality to automatically detect and record the occurrence of an injection event. In the absence of an automated system, a patient must manually keep track of the time of each injection. The inventors have thus recognized a need for a system that can automatically and accurately detect and record information about the occurrence of an injection event.

SUMMARY

The present disclosure relates to techniques for receiving injection event information from a medication delivery device. In some embodiments, the techniques can analyze contextual data associated with wirelessly-transmitted packets (e.g., advertising packets) to determine whether to (i) store injection event information (e.g., in a medication log on the computing device without prompting a user to confirm such storage), (ii) prompt a user for additional information (e.g., prompt a user to confirm whether to store the injection event information on the computing device), or (iii) ignore the wirelessly-transmitted packet (e.g., by taking no further action and not implementing either (i) or (ii)).

In one embodiment, the techniques provide for a computerized method that includes receiving, from a wireless communication interface of a medication delivery device, an advertising packet comprising injection event information generated by the medication delivery device, wherein the medication delivery device comprises (a) a reservoir configured to hold medication, (b) an actuating button for initiating an injection of the medication, and (c) a processing circuit in communication with the wireless communication interface, analyzing contextual data associated with the advertising packet to determine validation data, and determining, based on the validation data, whether to (i) include the injection event information in a medication log, (ii) prompt a user for additional information regarding the advertising packet, or (iii) ignore the advertising packet.

BRIEF DESCRIPTION OF DRAWINGS

The above mentioned and other features of this present disclosure, and the manner of attaining them, will become more apparent and the invention itself will be better understood by reference to the following description of embodiments of the present disclosure taken in conjunction with the accompanying drawings, wherein.

DETAILED DESCRIPTION

Figure 1:
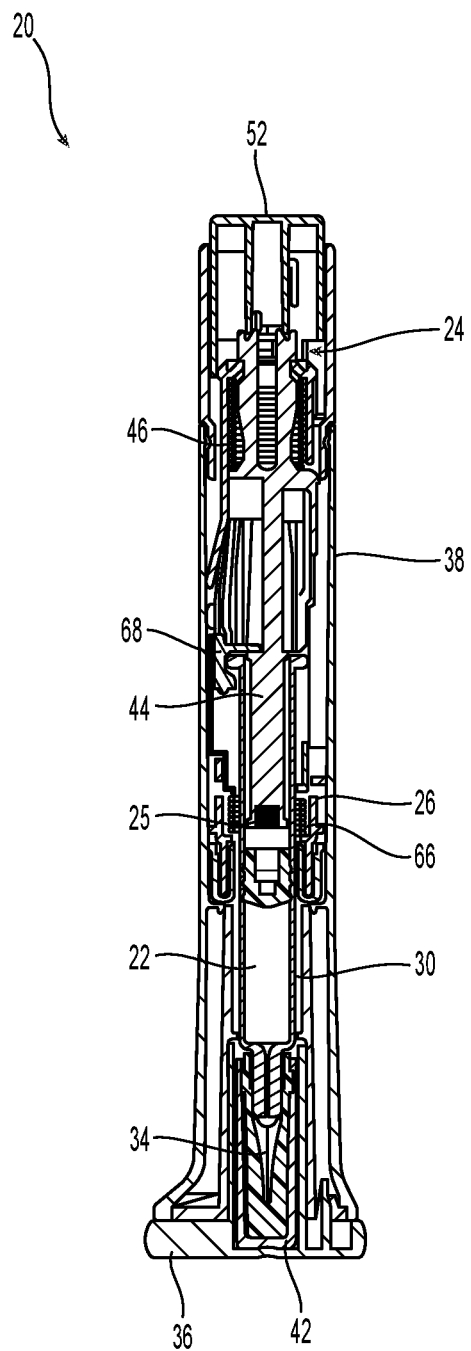
FIG. 1 is a cross sectional view of an injection device prior to use.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to software-based techniques for processing data received from a medication delivery device. According to some embodiments, the techniques can log information about medication that was delivered to a patient, such as a time of an injection event, a date of an injection event, a dose amount of the injection event, and/or other injection or dose-related data. Logging injection event information may help a patient to track dosing information over time. Such dosing information can be used, for example, to plan dosing schedules, such as to determine when to take their next dose of medication, which type of medication to take for their next dose, and/or how much of a medication to take for their next dose. Such dosing information can also be used by the patient's health care provider, payer, researcher conducting a clinical trial in which the patient is taking part, or other interested entity, to track patient's adherence to medication regimens over time. The inventors have appreciated that automatically logging injection data received from a medication delivery device can improve the accuracy and precision of the medication log and reduce the burden to the user, since the user no longer needs to manually keep track of such information. Since automatically logging dosing information may increase the accuracy of the medication log, automatic dose logging may help to improve patient adherence to a dosing regimen. In the context of a clinical trial, understanding more precisely when dosing occurs could help with efficacy analysis and determining appropriate dosing regimen. Furthermore, using such software-based techniques may enable a researcher to remotely access a medication log, eliminating the need for the patient to come to a centralized clinic, which may ultimately lead to shorter clinical trials and faster time-to-market. According to some embodiments, the techniques can receive the injection event information through wireless packets, such as advertising packets, broadcast by the medication delivery device. Many protocols for wirelessly communicating data between a transmitting device and a receiving device require a handshake or pairing procedure between the transmitting and receiving devices to establish a wireless communication link or session therebetween. However, as used herein, the term "advertising packets" is used to refer to wireless transmissions used by a transmitting device (e.g., a medication delivery device) to convey data to a receiving device (e.g., a computing device, such as a smartphone) without requiring any handshake or pairing process between the transmitting and receiving device. The inventors have appreciated that, by using advertising packets the user may not need to pair the medication delivery device and the computing device in order to process dose information from a medication delivery device. In particular, since pairing devices may require a user to perform multiple manual steps in order to complete the pairing process, avoiding such a pairing process can help to reduce the overall burden to the user. In addition, since pairing devices typically results in the computing device retaining a record of the previously-paired device to facilitate easier re-pairing in the future, avoiding such a pairing process can reduce usage of memory in the computing device—this may be particularly helpful if the user is expected to use many separate medication delivery devices over a relatively short period. The inventors have further appreciated that using advertising packets, such as Bluetooth Low Energy (BLE) advertising packets, may help to improve the battery life of a battery-powered medication delivery device, as opposed to other wireless communication options.

The inventors have appreciated that while there are benefits to using advertising packets that do not require a pairing process, relying on such packets can result in unintentional errors. For example, a computing device configured to process advertising packets with injection event information may erroneously receive an advertising packet from a different medication delivery device that is not associated with the user. For example, a patient who is in a public area may receive, on their mobile phone, an advertising packet from a medication delivery device belonging to another person who also happens to be using a similarly configured medication delivery device in the public area. As a result, automatically logging data included in received advertising packets may lead to errors in the medication log, such as logging data that is not associated with the patient. Consequently, the patient may miss a dose of medication and/or take a dose of medication at a time earlier than prescribed.

To address these and other issues, the techniques described herein can analyze contextual data associated with a received advertising packet to determine whether it was correctly received (e.g., from a medication delivery device belonging to the patient) or potentially erroneously received (e.g., from a different medication delivery device belonging to a different patient). In some embodiments, the contextual data may include information about the advertising packet, information about receipt of the advertising packet, and/or information about the medication delivery device from which the advertising packet was broadcast. For example, a user may typically take a dose of medication at certain time during the day. The computing device may analyze a time of receipt of the adverting packet to determine whether it aligns with the patient's typical dosing schedule. If the advertising packet is received at an atypical time, this may indicate that it was erroneously received from a different medication delivery device.

According to some embodiments, based on the analysis of the contextual data, the techniques can automatically process the injection event information (e.g., log the injection event information for the patent) or decide to either ignore the advertising packet or prompt the user for additional information to determine whether (or not) the received data should be processed for the user. In some embodiments, if it is likely that the advertising packet was correctly received from the patient's medication delivery device, then the computing device may automatically log the injection event information in the medication log without requiring further action by the user (e.g., without providing a validation prompt). As described above, automatically logging the information may minimize the burden on the patient. In some embodiments, if it is likely that the advertising packet was incorrectly received, then the computing device may either ignore the advertising packet or prompt the user to confirm whether to include the injection event information in the medication log. Preventing potentially incorrect information from being automatically included in the medication log may, for example, help to preserve the accuracy of the patient log, maintain the value of the patient log to the patient, and/or the like.

In an aspect, the medication delivery device includes a reservoir configured to hold a medication, an actuating button for initiating an injection of the medication, a wireless communication interface, and a processing circuit in communication with the wireless communication interface. The computing device is configured to receive, from the wireless communication interface of the medication delivery device, an advertising packet including injection event information generated by the medication delivery device, analyze contextual data associated with the advertising packet to determine validation data, and determine, based on the validation data, whether to (i) include the injection event information in a medication log or (ii) ignore the advertising packet or prompt a user for additional information regarding the advertising packet.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Figure 2:
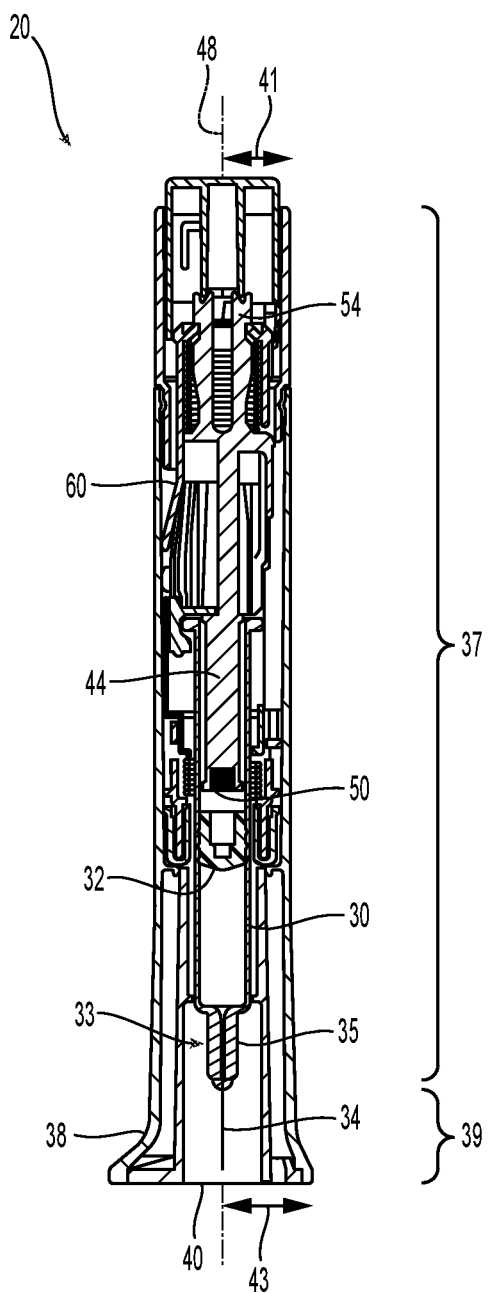
FIG. 2 is a cross sectional view of the injection device with the syringe assembly in a storage position and ready for an injection event.
Figure 3:
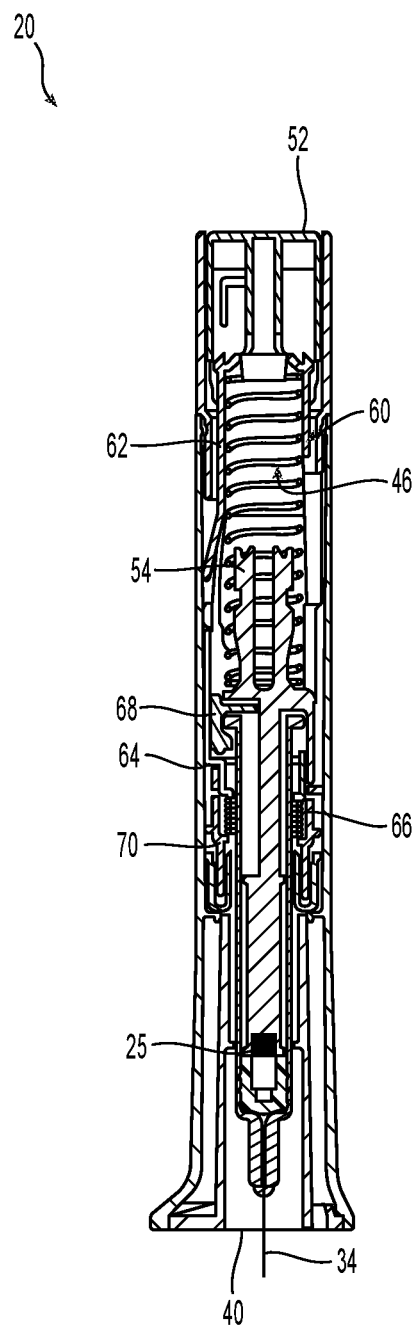
FIG. 3 is a cross sectional view of the injection device with the syringe assembly in an injection position.

An exemplary medication delivery device or medication injection device 20 is illustrated in various operational states in FIGS. 1-3. Examples of such a device and its operation are described in U.S. Pat. No. 8,734,394 B2, entitled Automatic Injection Device with Delay Mechanism Including Dual Functioning Biasing Member, issued May 27, 2014 to Adams et al. and in U.S. Patent Application Pub. No. 2021/0093784 A1, entitled Status Sensing Systems within an Injection Device Assembly, published Apr. 1, 2021 to Adams et al., the entire disclosure of both of which are hereby incorporated herein by reference. Device includes a syringe assembly 22, a drive mechanism 24, and a retraction mechanism 26, and may include one or more main printed circuit boards (PCBs) 82 and/or one or more secondary PCBs 84 shown later, for example, in FIG. 4. Syringe assembly 22 includes a barrel 30 forming a container body for holding a medication, and a piston 32 disposed within the barrel 30 for driving the medication outside the barrel. Syringe assembly 22 also includes a needle assembly 33 having a hollow injection needle 34 and a needle hub 35 which mounts needle 34 to syringe barrel 30. Advancing piston 32 within barrel 30 toward needle 34 dispenses medication through needle 34.

Devices described herein, such as device 20, may further comprise a medication, such as for example, within the syringe barrel 30. In another embodiment, a system may comprise one or more devices including device 20 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies including but not limited to IL-23 antibody analogs or derivatives, such as mirikizumab, IL-17 antibody analogs or derivatives, such as ixekizumab, therapeutic agents for pain-related treatments, such as galcanzeumab or lasmiditan, and any therapeutic agent that is capable of delivery by the devices described herein. The medication as used in the device may be formulated with one or more excipients. The device is operated in a manner generally as described above by a patient, caregiver or healthcare professional to deliver medication to a person.

Figure 4:
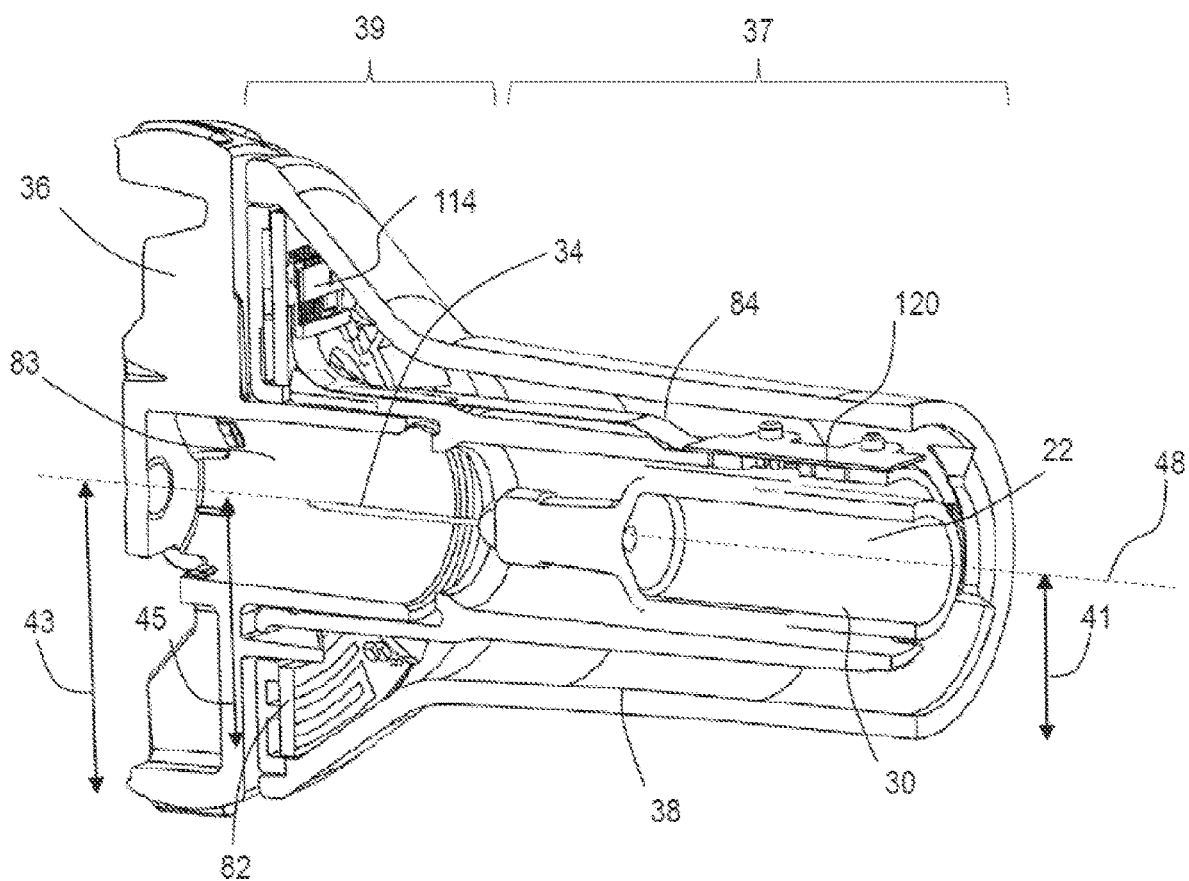
FIG. 4 is a cross sectional view of the injection device illustrating a placement of one or more main PCBs within an end portion of the injection device's housing.

FIG. 1 illustrates device 20 in its initial, pre-use configuration. Here, an end cap 36 is secured to an injection device housing 38 and covers a proximal end opening 40 in housing 38. As used herein, distal and proximal refer to axial locations relative to an injection site when the apparatus is oriented for use at such site, whereby, for example, proximal end of the housing refers to the housing end that is closest to such injection site, and distal end of the housing refers to the housing end that is farthest from such injection site. Housing 38 may be formed from a plastic material and is shown extending generally longitudinally between a distal end in close proximity to an actuating button 52 and a proximal end in close proximity to the proximal end opening 40 along a longitudinal axis 48. As shown in FIGS. 2 and 4, housing 38 may comprise a user-graspable portion 37 configured to be grasped by a hand of a user, the user-graspable portion 37 extending a radial distance 41 outward from longitudinal axis 48. In some embodiments, the radial distance 41 may be between 5-10 mm in length (e.g., in some embodiments, 5-8 mm may be a suitable length). Also as shown in FIGS. 2 and 4, housing 38 may also optionally comprise an outwardly-flared end portion 39 at a proximal end of the housing adjacent the proximal opening 40. The optional end portion extends a radial distance 43 outward from longitudinal axis 48 that is greater than the radial distance 41. In some embodiments, the radial distance 43 may be greater than 10 mm in length. For example, in some embodiments, the radial distance 43 may be between 10-20 mm in length (e.g., in some embodiments, 15-20 mm may be a suitable length). End portion 39 may slope smoothly radially outward from the user-graspable portion 37, as shown in FIGS. 1-3. In other embodiments, end portion 39 may take the form of other shapes. For example, end portion 39 may take on any shape that extends a radial distance 43 away from longitudinal axis 48 that is greater than the radial distance 41 of the user-graspable portion.

A needle guard 42 is mounted on syringe assembly 22 and covers and surrounds needle 34. End cap 36 and needle guard 42 protect the user from accidental needle pricks and also protect needle 34 from damage. When using device 20 to dispense medication, for example, injecting the medication into a patient, end cap 36 and needle guard 42 are first removed. FIG. 2 illustrates device 20 after removal of end cap 36 and needle guard 42 from syringe assembly 22, wherein the syringe assembly is in a storage position and device 20 is ready for a dispensing event.

Syringe assembly 22 is moveable relative to the injection device 20 between a storage position and an injection position. FIG. 3 illustrates device 20 after the syringe assembly 22 has been moved relative to device 20 to an injection position from its storage position that is shown in FIG. 2. In the storage position (FIGS. 1 and 2), needle 34 is retracted to a position such that needle 34 is disposed within housing 38 of device 20. In the injection position (FIG. 3), needle 34 projects outwardly from housing 38 beyond proximal opening 40 in the proximal direction parallel to longitudinal axis 48 whereby needle 34 may be inserted into a patient.

Drive mechanism 24 includes a plunger 44 which engages piston 32. Drive mechanism 24 includes a spring 46 that drives plunger 44 in a translational movement. In the illustrated embodiment, spring 46 advances plunger 44 along a linear path defined by the longitudinal axis 48 of device 20. As plunger 44 is advanced, foot 50 of plunger 44 contacts piston 32. As the plunger 44 is further advanced, syringe assembly 22 is advanced along axis 48 from its storage position to its injection position. After advancement of syringe assembly 22 to its injection position, the continued proximal advancement of plunger 44 advances piston 32 proximally within barrel 30 from its initial piston position (shown in FIGS. 1 and 2) to its final piston position (shown FIG. 3) to cause medication to be dispensed from needle 34 in a dispensing event. Prior to any dispensing of medication and when syringe barrel 30 holds the full original volume of medication, piston 32 will be in its initial piston position. After advancing piston 32 the full extent of its travel length toward needle assembly 33, piston 32 will be in its final piston position proximate needle assembly 33 and the medication from within barrel 30 will have been discharged. In a single use, syringe assembly 22 will hold a single dose of medication which will be delivered in a single injection event and piston 32 will be advanced from its initial piston position to its final piston position in that single injection event to thereby deliver the entire single dose contents of syringe assembly 22. While the device is shown as a single use device, device 20 may also be configured as a multiple-use device with appropriate modifications.

The advancement of plunger 44 will generally not result in the dispensing of medication from syringe assembly 22 until after syringe assembly 22 has been advanced to the injection position. There are factors that may inhibit the medication from being dispensed before the syringe is advanced to the injection position. A factor may be the friction between piston 32 and barrel 30. Typically, piston 32 will be formed out of a rubber material and barrel 30 will be glass. The frictional resistance between these two components may be sufficient to prevent the advancement of piston 32 within barrel 30 until syringe assembly 22 is advanced to its injection position and engagement with a suitable stop member prevents the further advancement of syringe assembly 22. Additionally, the medication within the syringe may be somewhat viscous and thereby somewhat resistant to flowing out of needle 34. If necessary, modification of piston 32 and syringe barrel 30 to alter the frictional resistance of dispensing motion of the engagement member 32 relative to syringe barrel 30 may limit or prevent the premature dispensing of medication before container 22 reaches its injection position.

To activate drive mechanism 24, a person depresses actuating button 52 at the distal end of device 20. Depressing button 52 disengages one or two elongate prongs 54 on plunger 44 from a shuttle assembly 60 thereby allowing spring 46 to axially advance plunger 44. Spring 46 has a helical shape and surrounds prongs 54. The proximal end of spring 46 biasingly engages flange 56 on plunger 44.

Shuttle assembly 60 may include an upper shuttle member 62 and a lower shuttle member 64. Shuttle members 62, 64 are fixed together in the final assembly. In the final assembly, upper shuttle member 62 captures button 52 and spring 46 limiting the axial movement of these parts in the distal direction. Prongs 54 engage surfaces on upper shuttle 62 when the device is in the condition shown in FIGS. 1 and 2. Depressing button 52 causes tabs on button 52 to engage ramps on prongs 54 to bias prongs 54 inwardly to disengage prongs 54 from upper shuttle member 62. After prongs 54 have been disengaged, spring 46 exerts a biasing force on flange 56 to advance plunger 44 from the position shown in FIG. 2 to the position shown in FIG. 3. As plunger 44 is advanced, it moves syringe assembly 22 to the injection position and then advances piston 32 to dispense medication as discussed above.

After the dispensing event is complete, retraction mechanism 26 optionally moves syringe assembly 22 from the injection position shown in FIG. 3 back to a retracted position. More specifically, the retraction mechanism is adapted to move the medication container from the injection position to the retracted position in a retraction movement. The retracted position may be similar to the storage position in that the syringe assembly is drawn back into the housing 38 such that needle 34 no longer projects proximally from proximal opening 40 and is disposed entirely within housing 38. In some embodiments, the retracted position may be the same as the storage position. In other embodiments, however, a syringe assembly 22 in the retracted position may be located slightly proximal or distal to a syringe assembly in the storage position. In the illustrated embodiment, the retraction mechanism includes a spring 66, a syringe carrier 68 and a rotary member 70 that acts as a follower. In yet other embodiments, the device 20 may include no retraction mechanism 26 such that the syringe assembly remains in its injection position indefinitely after the medication has been dispensed, until the syringe assembly is manually removed or repositioned by a user.

Plunger 44 may include an outrigger (not shown) which unlocks rotary member 70 as plunger 44 nears the end of its travel in the proximal direction. Rotary member 70 is rotationally secured to lower shuttle member 64 by engagement between a latch and a latching recess in lower shuttle member 64. The outrigger unlocks member 70 by depressing the latch. Spring 66 is torsionally preloaded and has one end engaged with member 70 and an opposite end engaged with shuttle assembly 60. Upon depression of the latch, spring 66 causes member 70 to rotate.

Member 70 is rotatable within housing 38 but is not axially moveable relative to housing 38. Other embodiments may include a member 70 that is also axially movable. The rotation of member 70 serves as a delay mechanism to prevent retraction mechanism 26 from retracting syringe assembly 22 until after the syringe assembly has finished delivering its dose of medication. The speed of rotation of member 70 may be adjusted by adjusting a viscosity of grease disposed on or around surfaces of member 70 that are in contact with housing 38—a more viscous grease results in slower rotation, while a less viscous grease results in faster rotation. A radial flange on rotary member 70 may engage a ledge within housing member 38 to limit the proximal movement of member 70. Spring 66 may exert an axial force, torsional force, or both forces on member 70 to bias member 70 proximally to thereby maintain member 70 in an axial position where the radial flange of member 70 engages the interior ledge of housing member 38.

Shuttle assembly 60 may include axially extending channels or ribs that engage corresponding features on housing member 38 that allow shuttle assembly 60 to move axially within housing 38 but which prevent the relative rotation of shuttle assembly 60 relative to housing member 38. Shuttle assembly 60 is biased in the distal direction by spring 66 but is prevented from moving distally by engagement of a latch (not shown) before activation of drive mechanism 24. When rotary member 70 completes its rotation, it disengages the aforementioned latch, thus allowing shuttle assembly 60 to move distally under the biasing force of spring 66.

As shuttle assembly 60 moves distally, it carries syringe assembly 22 distally and moves it back to the storage position shown in FIG. 2. Spring 66 biases the retraction mechanism 26 distally and thereby maintains syringe assembly 22 in its retracted position after an injection event. A locking mechanism such as a detent on the shuttle assembly 60 and a recess on the housing 38 member may additionally provide a locking engagement to secure syringe assembly 22 in the retracted position with needle 34 disposed within housing 38 after an injection event whereby the user may then dispose or otherwise handle device 20 in a safe manner.

Although FIGS. 1-3 depict and describe an exemplary drive mechanism 24 and an exemplary retraction mechanism 26, other mechanisms may also be used to drive syringe assembly 22 from the storage position to the injection position, and/or from the injection position to the retracted position. Such drive and/or retraction mechanisms may (but need not) include one or more springs or deformable parts that store energy when they are held in a pre-triggered state and, when triggered, release said stored energy to drive the syringe assembly from the storage position to the injection position, and/or from the injection position to the retracted position. Such mechanisms may (but need not) include mechanisms that generate motive force using chemical reactions or processes, e.g., by generating gas through the mixture of two or more reagents, or by igniting a small amount of combustible or explosive material. Such chemically-driven mechanisms may comprise one or more storage containers for the chemical reagents, a trigger that punctures or opens said storage containers, allows said reagents to mix, and/or which provides a spark or other ignition source for beginning the chemical reaction, and a movable piston or other component that moves in response to increasing gas pressure generated by the resulting chemical reaction. Such mechanisms may (but need not) include mechanisms that use stored electrical power (e.g., in a battery) to run electric motors that drive and/or retract the syringe assembly, or to trigger other physical or chemical mechanisms. Such mechanisms may (but need not) include hydraulic or pneumatic systems (e.g., tubes), gears, cables, pulleys, or other known components for transferring kinetic energy from one component to another. In some embodiments, rather than having separate mechanisms for driving the syringe assembly and then retracting the syringe assembly, a single mechanism may be configured to both drive and then retract the syringe assembly.

FIG. 4 illustrates an exemplary placement of one or more main PCBs 82 within the end portion 39, according to a first set of embodiments of device 20. The one or more main PCBs may be arranged perpendicular to the longitudinal axis 48, and may be stacked on top of each other, and/or may be arranged next to each other on the same plane perpendicular to the longitudinal axis 48. The main PCB(s) define an opening 83 through which injection needle 34 of syringe assembly 22 is configured to pass, for example, when end cap 36 is removed and the injection needle is driven proximally to inject the patient during a dispensing event. As shown, the main PCB(s) extend a radial distance 45 away from the longitudinal axis 48 that is greater than the radial distance 41 of the user-graspable portion 37. FIG. 4 also shows one or more secondary PCBs 84 that extend substantially perpendicular to the main PCBs and parallel to the longitudinal axis 48—secondary PCB(s) may be communicatively coupled to the main PCB(s) via one or more PCB connectors 114. While secondary PCB(s) 84 may mount additional sensing systems, such secondary PCBs are optional and may be excluded in certain embodiments to decrease manufacturing complexity and costs.

Figure 5A:
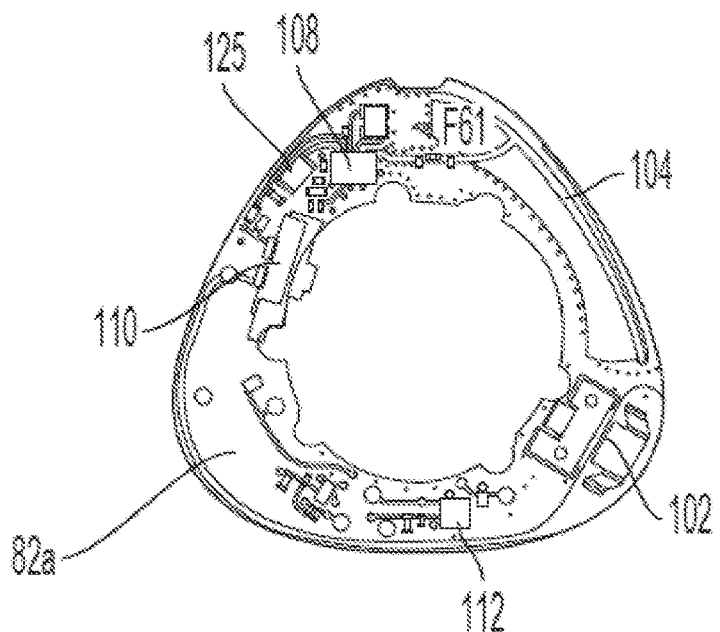
FIG. 5A is a top (i.e., distal) perspective view of a main PCB.
Figure 5B:
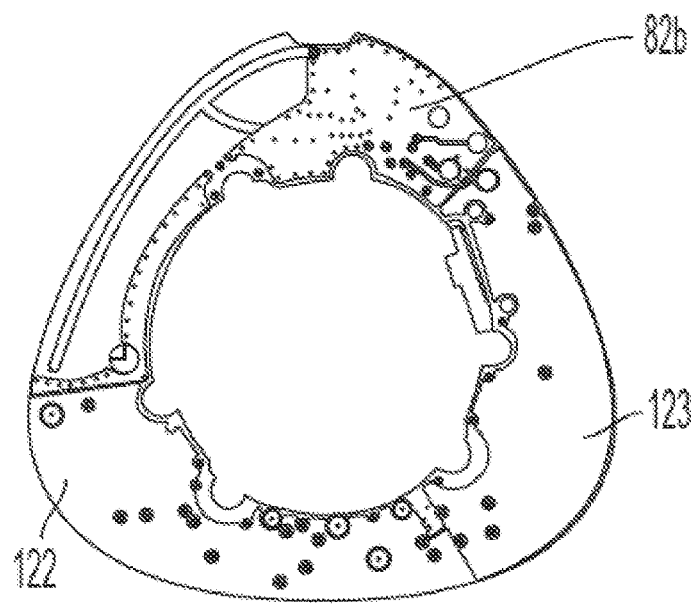
FIG. 5B is a bottom (i.e., proximal) perspective view of the main PCB.

FIGS. 5A and 5B illustrate another embodiment of main PCB(s) 82 which are not coupled to any secondary PCBs. FIG. 5A shows a top perspective view of the main PCB(s) 82, while FIG. 5B shows a bottom perspective view of the same PCB(s) 82, according to some embodiments of device 20. Main PCB(s) 82 comprises a top surface 82a (shown in FIG. 5A) and a bottom surface 82b (shown in FIG. 5B, top surface 82a and bottom surface 82b are understood to be part of PCB(s) 82). Top surface 82a includes or supports a power source 102 which, in some embodiments, may comprise a battery such as a coin cell battery mounted on battery clips (only the battery clips are depicted in FIG. 5A). Power source 102 provides electrical power to the electrical components integrated or coupled with injection device 20. An optional battery door (not shown) in housing 38 may hinge or swing open to allow access to power source 102. Main PCB(s) 82 may also include a processing circuit 108. In some embodiments, processing circuit 108 may take the form of a System on Chip (SOC) integrated circuit that includes a processor, memory, and input/output ports. However, processing circuit 108 may also be implemented using other types of components, such as a microcontroller (MCU), or an Application Specific Integrated Circuit (ASIC). Processing circuit 108 may be configured to execute computer-executable instructions stored on non-transitory storage media. Main PCB(s) 82 may also include or be communicatively coupled to a plurality of different types of sensors, such as a basecap removal sensor 110, an accelerometer 112, a temperature sensor 125, and/or one or more capacitive pad(s) 122 and 123.

Basecap removal sensor 110 may allow processing circuit 108 to detect whether basecap 36 is attached to housing 38, or has been removed by a user. Basecap removal sensor 110 may be communicatively or electrically coupled with processing circuit 108.

Accelerometer 112 may detect shocks or accelerations caused by initiation of a dispensing event in which syringe assembly 22 is driven by drive mechanism 24 from the storage position to the injection position. Accelerometer 112 may also detect shocks or accelerations caused by a retraction movement upon completion of the dispensing event in which syringe assembly 22 is driven by the retraction mechanism 26 from the injection position to the retracted position. Accelerometer 112 may send an output signal to processing circuit 108 via one or more electrical connections to allow processing circuit to analyze the output signal.

In some embodiments, processing circuit 108 may analyze the signal output from accelerometer 112 to determine a certain condition or state of the device 20, or to detect the occurrence of a certain event or action. For example, processing circuit 108 may analyze the output signal to discern when the basecap 36 has been removed, or when the actuation button 52 has been unlocked. Processing circuit 108 may also be configured to determine when a dispensing event is initiated or completed based on signals from accelerometer 112, either alone or in conjunction with signals from one or more skin contact sensors.

When a dispensing event is initiated, drive mechanism 24 is activated to drive the syringe assembly 22 from the storage position to the injection position. This driving motion imparts one or more accelerations that may be detected in the signal output from accelerometer 112. For example, the pushing force imparted by drive mechanism 24 as it drives syringe assembly 22 from the storage position in the proximal direction may cause accelerometer 112 to detect an acceleration in the distal direction along longitudinal axis 48. When syringe assembly 22 hits its stopping position at its injection position at the end of this driving motion, the sudden stop of syringe assembly 22 may cause accelerometer 112 to detect an acceleration in the proximal direction along longitudinal axis 48. Either this proximal or distal acceleration (or both) may cause accelerometer 112 to output a first acceleration spike that may be detected by processing circuit 108. This first acceleration spike may be indicative of initiation of a dispensing event.

Similarly, when a dispensing event has been completed, the retraction mechanism 26 is activated to drive the syringe assembly 22 from the injection position to the retracted position. This driving motion imparts one or more accelerations that may also be detected in the signal output from accelerometer 112. For example, the pushing force imparted by retraction mechanism 26 as it drives syringe assembly 22 from the injection position in the distal direction may cause accelerometer 112 to detect an acceleration in the proximal direction along longitudinal axis 48. When syringe assembly reaches the retracted position, the sudden stop of syringe assembly 22 may cause accelerometer 112 to detect an acceleration in the distal direction along longitudinal axis 48. Either this proximal or distal acceleration (or both) may cause accelerometer 112 to output a second acceleration spike that may be detected by processing circuit 108. This second acceleration spike may be indicative of completion of the dispensing event. As used herein, an "acceleration spike" is defined as any artifact in an acceleration or vibration signal output by an accelerometer or vibration sensor (e.g., a piezo sensor) that is indicative of initiation and/or completion of a dispensing event.

Many types of medication need to be stored at a first, relatively cool temperature (e.g., between 36 and 46 degrees Fahrenheit, or 2 and 8 degrees Celsius) to prevent spoliation, but then need to be warmed up to a second, warmer temperature (e.g., to room temperature, or between 65 and 75 degrees Fahrenheit, or 18 and 24 degrees Celsius) before being injected into the patient's body. To ensure that the medication within barrel 30 is stored at the appropriate storage temperature, and/or to ensure that the medication is warmed to the appropriate injection temperature, injection device 20 may be equipped with a mechanism for estimating the temperature of the medication. By ensuring that the medication has warmed up to the appropriate temperature, this information can be transmitted to a phone, or the device itself could signal a patient that the device is ready for use. In some embodiments, this temperature-measurement function may be performed by a temperature sensor 125 directly mounted on the main PCB(s) 182 to estimate the temperature of the medication. This temperature sensor may be communicatively or electrically coupled to processing circuit 108, and outputs a temperature output signal that is received and analyzed by the processing circuit. In one example, the temperature sensor 125 is mounted to the distal surface of PCB, and in some instances, disposed circumferentially spaced from the pads 122, 123.

Temperature sensor 125 may comprise any of a plurality of types of temperature sensors that may be mounted on a PCB, such as but not limited to a thermistor (e.g., a negative temperature coefficient (NTC) thermistor, or a resistance temperature detector (RTD)), a thermocouple, or a semiconductor-based temperature sensor. Temperature sensor 125 may be configured and positioned to measure a temperature of a thermal ballast. The thermal ballast may comprise all or a portion of the silicon substrate of main PCB(s) 82 itself. Alternatively, the thermal ballast may comprise a suitable heat sink comprised of other materials (e.g. a polymer) that is mounted on main PCB(s) 82. The thermal ballast may be is in contact with, or surround all or a portion of, temperature sensor 125.

Near Field Communication (NFC) or Bluetooth Low Energy (BLE) connectivity may be provided by one or more antennas 104 mounted on the PCB(s) 82. Such antennas 104 may receive signals from processing circuit 108 that cause the antennas to send wireless communications to external devices. Although FIG. 5A depicts only one antenna 104, some embodiments may comprise two or more antennas, e.g., one BLE antenna and a separate NFC antenna. In some embodiments, processing circuit 108 may itself comprise an integrated BLE antenna, while antenna 104 may comprise an NFC antenna. Some embodiments may also use chip antennas instead of PCB trace antennas as depicted.

Main PCB(s) may also be communicatively coupled or integrated with a plurality of sensors that detect contact with skin tissue. Skin contact sensors may be used to verify proper contact with the user's skin before the user activates injection device 20. Injection device 20 may also indicate to the user which sensors detect skin contact and which do not; this lets the user know which way he or she should tilt or move the injection device 20 before injection. This functionality decreases the likelihood of failed injections in which the needle 34 fails to penetrate the skin of the user, or penetrates at an improperly shallow angle.

FIG. 5B depicts an exemplary embodiment that includes two capacitive pads 122 and 123 to detect skin contact. Pads 122, 123 are shown as discrete planar structures disposed along the distal surface of the PCB. Capacitive pads 122 and 123 may be configured to detect proximity of human tissue by such tissue's effect on an electrical field created by the sensor, e.g., by measuring the effect of such human tissue on the capacitance of an electrical circuit being monitored or measured by the sensor. Capacitance sensors do not require a metallic, electrical terminal that directly contacts skin tissue, and so may be partially or completely sealed behind a protective, non-conducting cover (e.g., made of plastic). This may increase the durability of the capacitance sensor by decreasing seepage of moisture or foreign substances into sensitive electrical components. Capacitance sensors may also reduce the danger of electrostatic discharge damaging sensitive electrical components within the device, since capacitance sensors do not require exposed metallic contacts. Capacitive pads 122 and 123 may each individually detect contact with skin tissue, such that processing circuit 108 may determine when one pad detects contact but the other does not. Although FIG. 5B depicts two capacitive pads 122 and 123, other embodiments may have less or more capacitive pads. For instance, main PCB(s) 82 may include only a single capacitive pad, or it may have three, four, five, six, or more capacitive pads.

Figure 6:
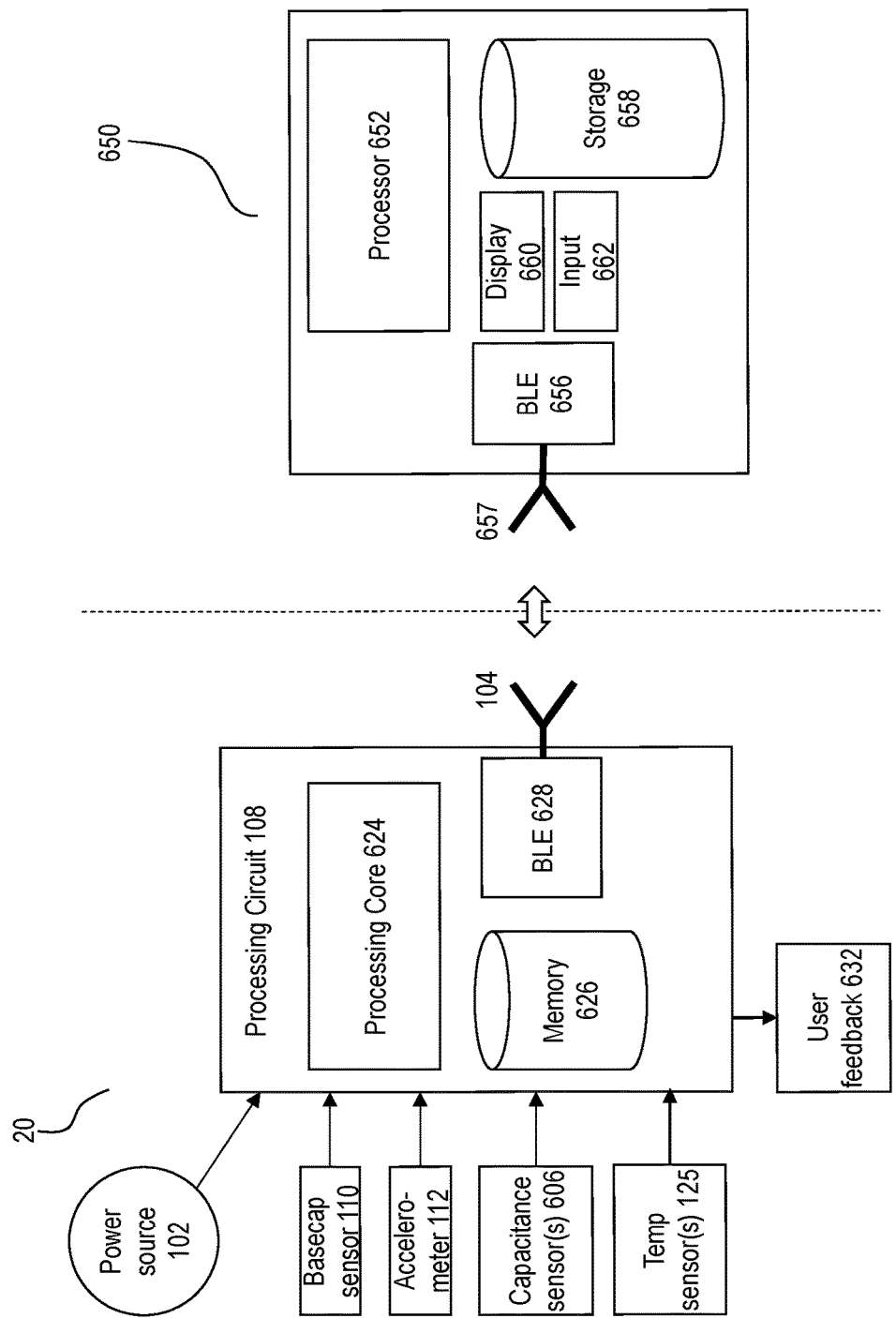
FIG. 6 is a system architecture view of electrical components within the injection device and of an external device.

FIG. 6 provides a system architecture view of the electrical components within device as well as a communication link with an exemplary external device 650, according to some embodiments of device 20. Some or all of these components may be mounted on main PCB(s) 82, previously depicted in FIGS. 5A and 5B. As previously-discussed and depicted in the aforementioned figures, these electrical components may comprise a processing circuit 108. In some embodiments, processing circuit 108 may take the form of a Bluetooth Low Energy (BLE) System on Chip (SOC). Such a BLE SOC may comprise a chip including processing core 624 (e.g., a mini-processor or arithmetic logic unit (ALU)), on-board memory 626 (e.g., non-transitory computer-readable media, such as volatile or non-volatile memory) used to store programming instructions executed by the processing core 624, and a BLE circuit 628 and BLE antenna 630. In some embodiments, as previously discussed, BLE circuit 628 and BLE antenna 630 may be replaced or supplemented with a NFC communications circuit and/or antenna. Processing circuit 108 is configured to control and coordinate the functions of the electrical components depicted in FIG. 6. Processing circuit receives power from power source 102.

Processing circuit 108 may be communicatively coupled with multiple electrical components, including basecap removal sensor 110, accelerometer 112, temperature sensor 125, and/or one or more touch sensor(s) 606.

Touch sensor(s) 606 may take the form of capacitive pads 122 and 123, as previously-depicted and described in FIG. 5B. However, touch sensor(s) 606 may also take the form of any other type of sensors configured to detect contact with skin tissue, such as electric resistance sensors, for example.

Accelerometer 112 may take the form of any circuitry configured to detect shocks, vibrations, and/or accelerations associated with the initiation and/or completion of a dispensing event, as previously-described. For example, accelerometer 112 may take the form of an accelerometer configured to detect accelerations along one, two, or three axes, or it may take the form of a piezo vibration sensor.

Basecap sensor 110 may take the form of a physical, electrical, optical, and/or magnetic sensor that detects whether basecap 36 is attached to housing 38 or has been removed by the user. Temperature sensor 125 may comprise any of a plurality of types of temperature sensors that may be mounted on a PCB, as described previously. Processing circuit 108 may also optionally be connected to a device 632 for providing user feedback that is integrated with device 20. The means for user feedback may include one or more indicator lights, e.g., implemented using light-emitting diodes (LEDs), a display, a haptic indicator such as a vibration motor, and/or an auditory indicator such as speaker.

Processing circuit 108 may be communicatively coupled with each of the aforementioned components via one or more physical, electrical channels. In some cases, signals received by the processing circuit 108 may be converted from an analog to a digital signal using an analog-to-digital converter (ADC), not shown.

Processing circuit 108 may be configured to allow injection device 20 to communicate wirelessly with an external device (such as, for example, a mobile phone, a wearable device, a laptop, and/or server database). For example, BLE circuit 628 and BLE antenna 104 may allow processing circuit 108 to send wireless BLE advertising packets to an external device 650.

FIG. 6 also shows an exemplary external device 650 that is physically separate from injection device 20. In this embodiment, exemplary external device 650 may take the form of a mobile smartphone having a processor 652 (e.g., a microprocessor or CPU) and storage 658. Storage 658 may comprise non-transitory computer-readable media storing computer-executable instructions that, when executed by processor 652, causes device 650 to perform the operations described herein. These computer-executable instructions may comprise a mobile application, such as a medical mobile application. Device 650 may further comprise a display 660 and a user input device 662. User input device 662 may comprise physical buttons or switches integrated with the smartphone. Although depicted separately in FIG. 6, all or a portion of user input device 662 may be integrated with display 660, e.g., in a touch-sensitive screen.

Device 650 may be configured to establish a wireless communication link with injection device 20. For example, external device 650 may include a BLE circuit 656 coupled with a BLE antenna 657, which communicates with processing circuit 108.

Further details of the design and operation of an exemplary medication delivery device 20 may be found in U.S. Patent Application Pub. No. 2021/0093784 A1, entitled Status Sensing Systems Within an Injection Device Assembly, the entire disclosure of which is hereby incorporated by reference herein.

As described herein and in conjunction with FIGS. 5A and 5B, the medication delivery device may be configured to generate data about a state of the device or about the occurrence of a certain event or action. For example, a processing circuit of the medication delivery device may analyze a signal from an accelerometer to determine when an injection event has been initiated and/or completed. As another example, the processing circuit may analyze a signal from a skin contact sensor to verify proper contact with the user's skin prior to the initiation of an injection event. In some embodiments, the data may include information about the time of an injection event, the time that has elapsed since an injection event, the date of injection event, the temperature of a medication stored in the medication delivery device, the state of the skin contact sensors, or any other suitable data, as aspects of the techniques described herein are not limited in this respect.

In some embodiments, the generated data is provided to a computing device (e.g., external device 650), such that the computing device can be used to monitor injection event activity and/or the condition of the medication delivery device. For example, a mobile application on the computing device may be used to log data (e.g., injection event information) received from the medication delivery device, such as the time and/or date of an injection event. In some embodiments, this may help a user to adhere to an injection regimen, since the injection event information is automatically and accurately logged.

According to some embodiments, the medication delivery device may communicate with the computing device by broadcasting advertising packets (e.g., Bluetooth Low Energy (BLE) advertising packets) that contain the injection event information. For example, upon delivering a dose of medication, the medication delivery device may begin to broadcast advertising packets that contain the time and/or date of the injection event. In some embodiments, a mobile application on the computing device may automatically receive and log the injection event information. In some embodiments, as described herein, the use of such advertising packets may eliminate the need to pair the devices, which can be burdensome to the user. For example, if two devices are communicating using Bluetooth, part of the Bluetooth pairing process can require a user to perform multiple steps to complete the pairing process, which may be time-consuming and/or confusing to patients that are not computer-savvy.

However, due to the lack of a pairing process, the advertising packets may be erroneously (and unintentionally) received by a different computing device. For example, a patient may receive, on their mobile device, advertising packets from a medication delivery device that belongs to a different user. Automatically logging injection event information contained in those advertising packets may interfere with the patient's injection regimen. Therefore, rather than automatically logging injection event information upon receiving an advertising packet, the computing device may be configured to analyze contextual data associated with the received advertising packet (e.g., at the application level), according to the techniques described herein, to avoid logging incorrect information. In some embodiments, the contextual data may be used to determine whether to automatically log the injection event information or to prompt the user for more information (e.g., to confirm whether to log the injection event information if there is a chance the received data is not associated with the patient). In some embodiments, the contextual data may be used to determine whether to ignore the received advertising packet by taking no action, i.e., neither logging the injection event information nor prompting the user for more information.

While some examples provided herein refer to processing BLE advertising packets, it should be appreciated that the techniques can be used to process any wireless packet without departing from the spirit of the techniques described herein. For example, other types of packets that can be processed according to the techniques described herein include packets from any suitable wireless or cellular communication protocols, such as WiFi, Long Range (LoRa), NFC, Radio-Frequency Identification (RFID), Ultra-Wideband (UWB), Matter, Long Term Evolution CAT M1 (LTE-M), Narrowband-Internet of Things (NB-IoT), and 4G.

Therefore, such examples are provided for illustrative purposes only and are not intended to limit the techniques described herein.

Figure 7:
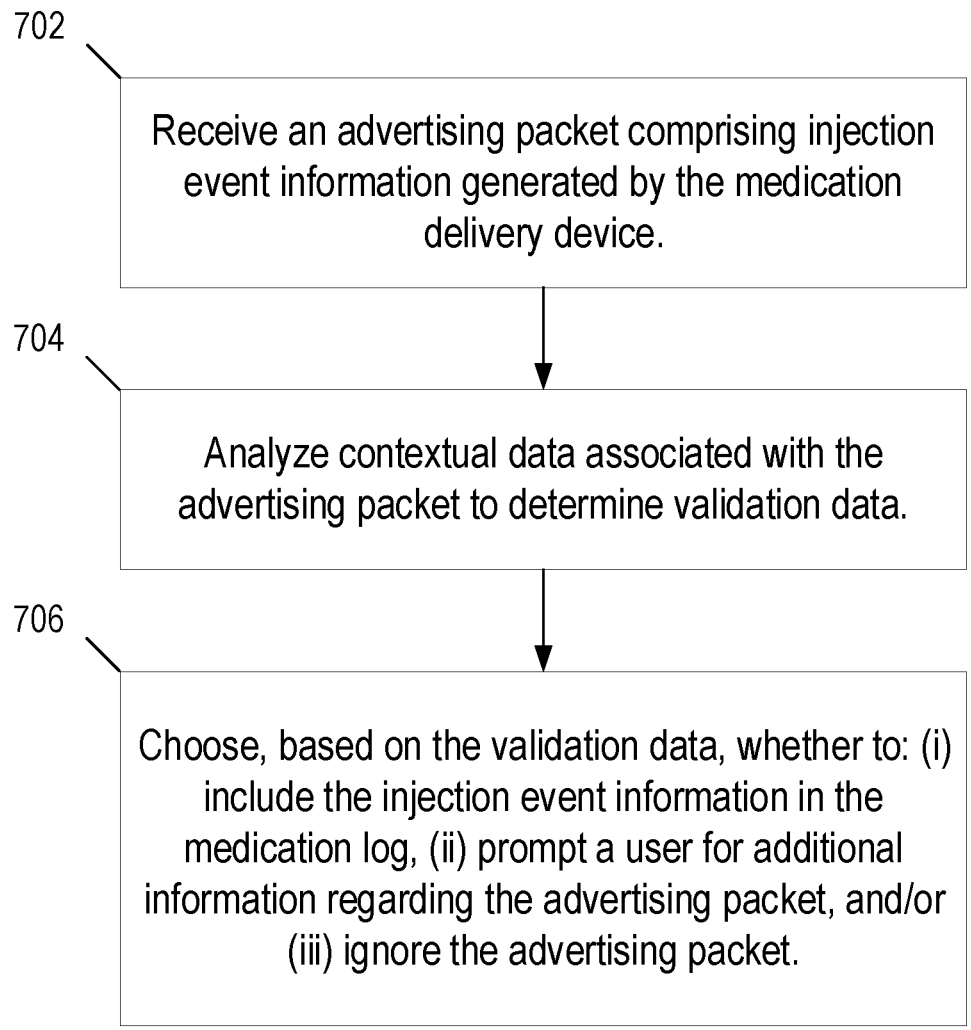
FIG. 7 is a flowchart showing an exemplary computerized method 700 for determining whether to log data included in an advertising packet received from a medication delivery device.

FIG. 7 is a flowchart showing an exemplary computerized method 700 for determining whether to log data included in an advertising packet received from a medication delivery device, according to some embodiments. At step 702, a computing device receives, from a wireless communication interface of the medication delivery device, an advertising packet including injection event information generated by the medication delivery device. In some embodiments, the advertising packet is received by a program running on the computing device, such as a mobile application. In some embodiments, the injection event information may include information about when a dose of medication was delivered to a user, such as the time of an injection event, the time elapsed since the injection event, and/or the date of the injection event. In some embodiments, the medication delivery device may include embodiments of device 20, described in conjunction with FIGS. 1-6. For example, the wireless communication interface may include antennas 104 of device 20.

At step 704, the computing device analyzes contextual data associated with the advertising packet to determine validation data. In some embodiments, the contextual data may include information about the advertising packet, information about receipt of the advertising packet, and/or information about the medication delivery device that broadcast the received advertising packet. In some embodiments, the contextual data may be analyzed to determine validation data, or data that is indicative of whether the advertising packet was erroneously received by the computing device. In some embodiments, this may include comparing the contextual data to a set of criteria to determine the validation data.

At step 706, the computing device determines, based on the validation data, whether to (i) include the injection event information in a medication log, (ii) prompt a user for additional information regarding the advertising packet, and/or (iii) ignore the advertising packet. In some embodiments, if the validation data indicates that the advertising packet was correctly received (e.g., the advertising packet was received from the correct medication delivery device), then the injection event information may be included in the medication log. In some embodiments, if the validation data indicates that the advertising packet may have been erroneously received (e.g., the advertising packet was received from a different medication delivery device), then the computing device may prompt the user for additional information. In some embodiments, this may include prompting the user (e.g., with a notification on a display of the computing device) to confirm whether to log the injection event information in the medication log. This may enable a user to easily add injection event information to their medication log, while preventing incorrect injection event information from interfering with their injection regimen. In some embodiments, if the validation data indicates that there is a high probability that the advertising packet was erroneously received, then the computing device may ignore the advertising packet by neither including the injection event information in the medication log, nor prompting the user for additional information. In this scenario, ignoring the advertising packet may also comprise the computing device deleting the advertising packet from its memory, and/or configuring itself to ignore future advertising packets from the medication delivery device that sent the advertising packet. In some embodiments, step 706 may consist of choosing between only two of options (i) (include the injection event information in a medication log), (ii) (prompt the user for additional information regarding the advertising packet), and (iii) (ignore the advertising packet) based on the validation data. For example, in some embodiments, step 706 may consist of choosing between only between options (i) and (ii), only between options (i) and (iii), or only between options (ii) and (iii) based on the validation data.

Figure 8:
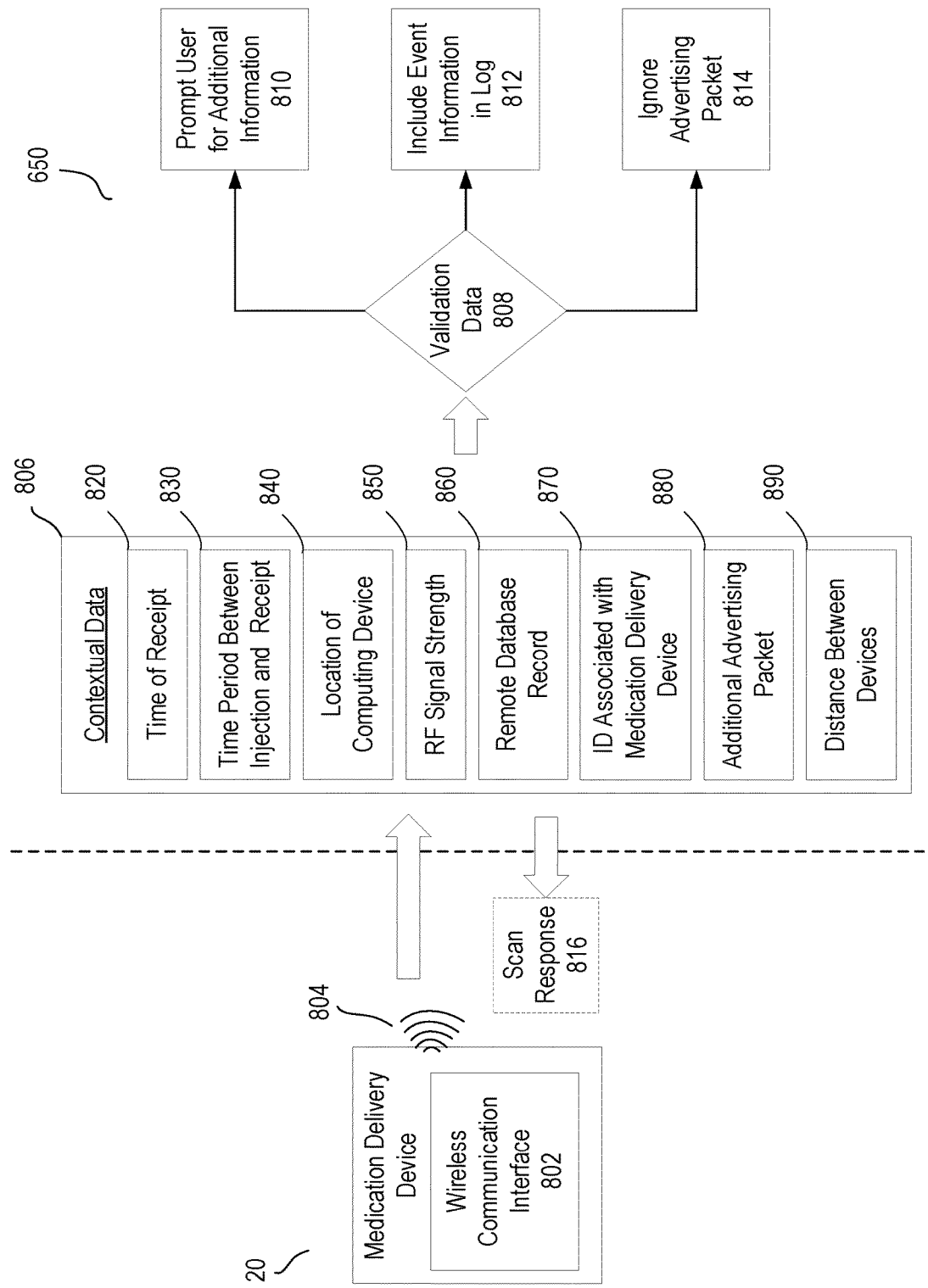
FIG. 8 shows a diagram of an example system for determining whether to (i) log data included in an advertising packet received from a medication delivery device, (ii) prompt user for additional information, and/or (iii) ignore the advertising packet, according to some embodiments.

FIG. 8 shows a diagram of an example system for determining whether to (i) log data included in an advertising packet received from a medication delivery device, (ii) prompt user for additional information, and/or (iii) ignore the advertising packet, according to some embodiments. As shown, computing device 650 receives advertising packet 804 from the wireless communication interface 802 of medication delivery device 20. In some embodiments, the advertising packet 804 may be broadcast from one or more antennas of the wireless communication interface 802, such as antennas 104. In some embodiments, the advertising packet may include injection event information generated by the medication delivery device 20, which may include information about the time and/or date of a dose of medication delivered to a user.

In some embodiments, after receiving the advertising packet, computing device 650 may optionally issue a scan response 816. In some embodiments, a scan response may indicate to the medication delivery device 804 that the advertising packet was received by the computing device 650. In some embodiments, the scan response 816 may be configured to cause the medication device to perform one or more functions. For example, upon receiving the scan response 816, the medication delivery device 804 may power down.

According to some embodiments, the computing device 650 may analyze contextual data 806 associated with the advertising packets to determine validation data 808. As described herein, including with respect to FIG. 7, the contextual data 806 may include information about the advertising packet, information about receipt of the advertising packet, and/or information about the medication delivery device from which the advertising packet was broadcast. FIG. 8 shows examples of different types of contextual data. As shown, the contextual data may include the time of receipt of the advertising packet (item 820), the time period between the injection event and the receipt of the advertising packet (item 830), the location of the computing device upon receipt of the advertising packet (item 840), a strength of the radio frequency (RF) signal of the advertising packet (item 850), an indication, from a remote database, of whether another computing device has already received advertising packets from the medication delivery device (item 860), an identifier (ID) associated with the medication delivery device (item 870), information indicative of an additional advertising packet received by the computing device (item 880), the distance between the computing device and the medication delivery device (item 890) and/or any suitable combination of contextual data types (e.g., any combination of items 820, 830, 840, 850, 860, 870, 880, and 890 and/or other data not shown in FIG. 8). It should be appreciated that the list of provided examples of contextual data is a non-exhaustive list, and may include any suitable type of contextual data, as aspects of the techniques described herein are not limited in this respect.

In some embodiments, the validation data 808 may provide an estimate of whether the advertising packet 804 was correctly (or incorrectly) received by the computing device 650. In some embodiments, analyzing the contextual data 806 may include comparing the contextual data to specified criteria to determine the validation data 808. Examples of analyzing different types of contextual data are described herein, including with respect to FIGS. 9-15. In some embodiments, one type of contextual data 806 may be used to determine the validation data 808. For example, the computing device 650 may compare the time of receipt (item 820) to specified criteria (e.g., a threshold time) to determine the validation data 808. In other embodiments, a combination of types of contextual data 806 may be used to determine the validation data 808. For example, the computing device may compare the strength of an RF signal of the advertising packet (item 850) to first criteria (e.g., a threshold strength) and the time of receipt (e.g., a threshold time) to second criteria. Based on the combination, the computing device may determine validation data 808.

According to some embodiments, determining validation data 808 based on a combination of types of contextual data 806, may include comparing each type of contextual data to criteria (e.g., a threshold) and combining the results using a logic algorithm. For example, the results may be combined using a fuzzy logic algorithm (e.g., weighted or unweighted) to determine whether or not the advertising packet may have been erroneously received by the computing device. In some embodiments, using a weighted algorithm to combine the results of the analysis allows for each type of contextual data to be weighted with a different degree of important. For example, contextual data that may result in a more reliable estimate of whether or not an advertising packet was erroneously received may be weighted with a greater degree of importance than other types of contextual data.

According to some embodiments, based on the validation data 808, the computing device 650 may determine whether to (i) include the injection event information in the medication log 812, (ii) prompt a user for additional information 810, and/or (iii) ignore the advertising packet 814. In some embodiments, if the validation data indicates that the advertising packet 804 may have been erroneously received from the medication delivery device 20, then the computing device 650 may prompt the user for additional information 810. For example, the computing device 650 may provide a notification on a display of the computing device 650, prompting the user to confirm whether to include the injection event information in the medication log. In some embodiments, if the validation data indicates that there is a high probability that the advertising packet 804 was erroneously received from the medication delivery device 20, then the computing device 650 may ignore the advertising packet 814. In some embodiments, if the validation data 808 indicates that the advertising packet 804 may have been correctly received by the computing device 650, then the computing device 650 may automatically include the injection event information in the medication log 812. It should be understood that while FIG. 8 depicts an embodiment in which the validation data is used to select between three courses of action (i), (ii) and/or (iii), in some embodiments the validation data may be used to select between only two courses of action, e.g., any two of options (i), (ii), and (iii).

FIGS. 9-16 are example flowcharts for analyzing different types of contextual data to determine whether to include the injection event information in the medication log or to prompt the user for additional information, according to some embodiments.

Figure 9:
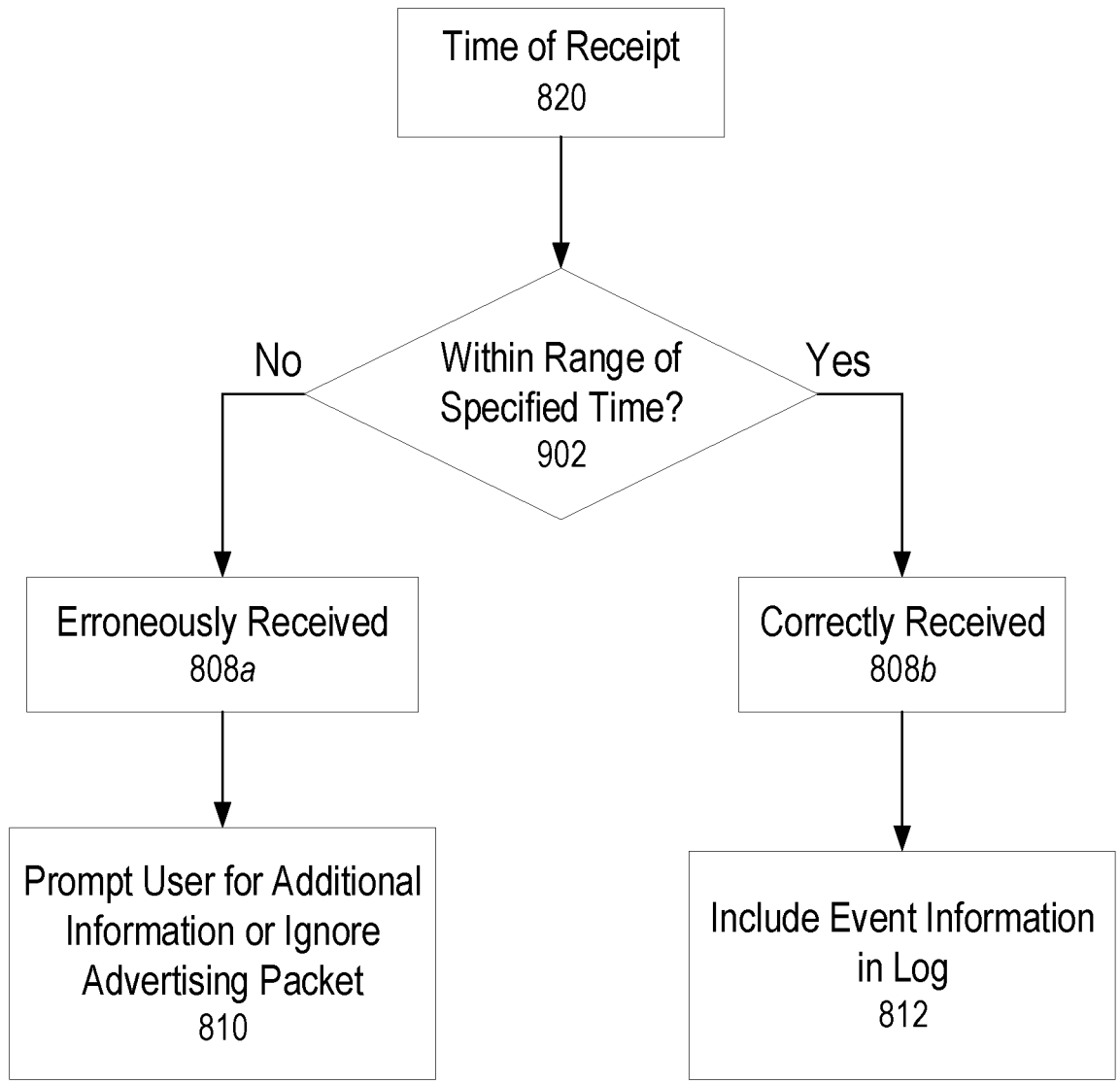
FIG. 9 is an example flowchart for analyzing the time at which the computing device receives an advertising packet.

FIG. 9 is an example flowchart for analyzing the time at which the computing device receives an advertising packet, according to some embodiments. At step 902, the time of receipt (item 820) is analyzed to determine whether it is within a range of a specified time. In some embodiments, the specified time may be one or more times at which the user typically takes his or her dose of medication. For example, a user may take a dose of medication around mealtimes. If the computing device receives an advertising packet at a time that is close to when the user typically takes a dose of medication, then this may indicate that the advertising packet was correctly received (e.g., validation data 808b) by the computing device. If the computing device receives an advertising packet at a time that is atypical for the user to take a dose of medication, then this may indicate that the advertising packet was erroneously received (e.g., validation data 808a) by the computing device.

According to some embodiments, the specified time and/or the range of times may be pre-set by a user. For example, the user may indicate (e.g., by interacting with a user interface of the computing device) the times or range of times at which they typically take a dose of medication. In some embodiments, the time or range of times is automatically determined based on past injection times included in the medication log. For example, a machine learning model may be trained using the data included in the medication log. Based on the time of receipt (item 820), the trained machine learning model may automatically determine whether or not the advertising packet may have been correctly (or erroneously) received.

Based on the validation data 808a and 808b, the computing device determines whether to prompt the user for additional information or ignore the advertising packet 810 or to include the injection event information in the medication log 812. As described herein, if the time of receipt (item 820) is not within range of the specified time, then the computing device may determine that the advertising packet was erroneously received (validation data 808a) and prompt the user for additional information or ignore the advertising packet 810. Alternatively, if the time of receipt (item 820) is within range of the specified time, then the computing device may determine that the advertising packet was correctly received (validation data 808b) and include the injection event information in the medication log 812.

In some embodiments, the flowchart depicted in FIG. 9 may be modified to allow the computing device to choose between not just two courses of action, but three courses of action. For example, if the time of receipt is within a first range of an expected time(s), the computing device may determine that the packet was likely to be correctly received and will include the dose event information in the log. If the time of receipt is not within the first range of the expected time(s) but is within a second range of the expected time(s) (wherein the second range is broader than the first range), the computing device may determine that the packet may have been incorrectly received and will prompt the user for additional information. If the time of receipt is neither within the first range nor the second range of the expected time(s), the computing device may determine to ignore the advertising packet.

Figure 10:
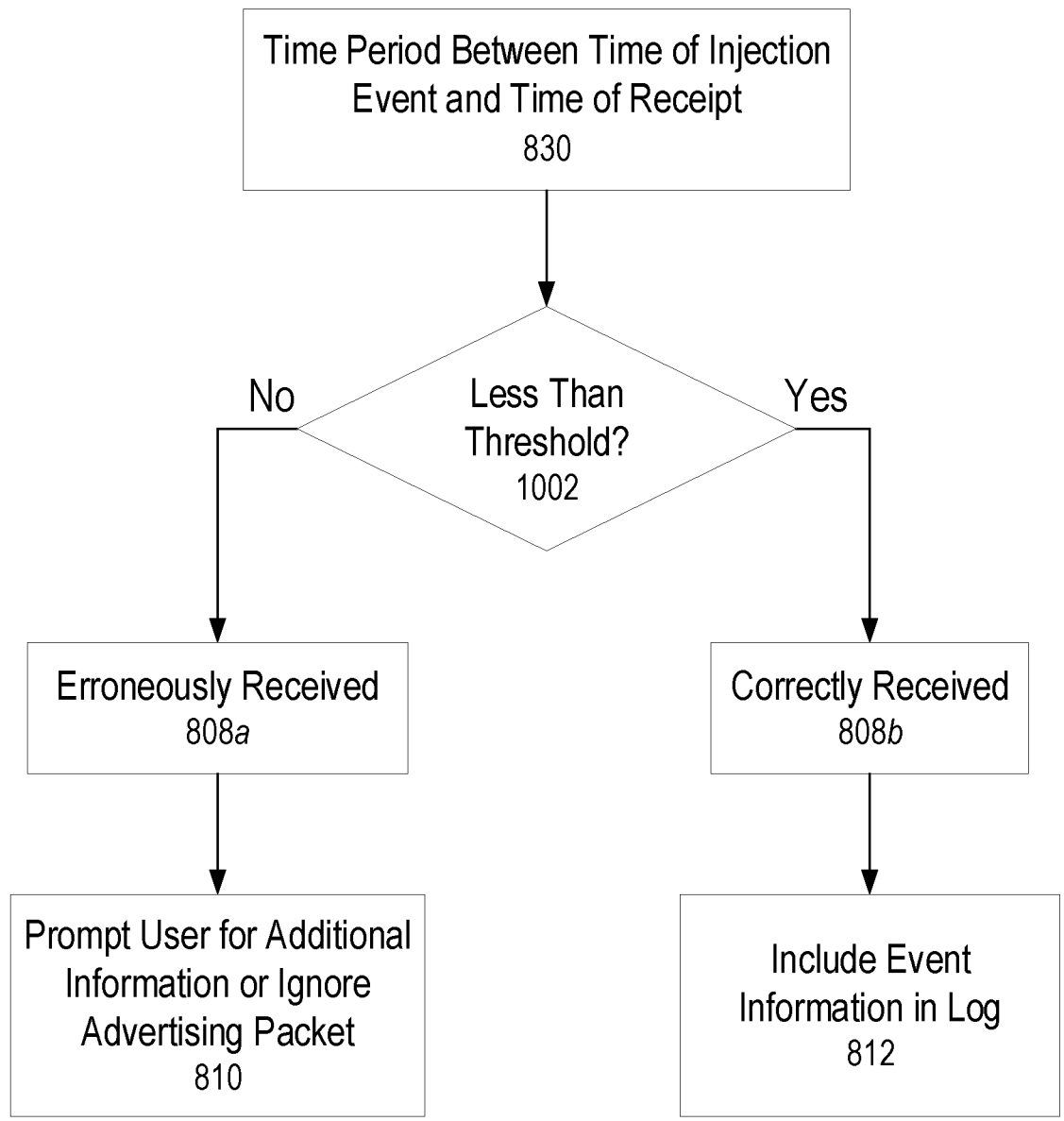
FIG. 10 is an example flowchart for analyzing the time period between the time of the injection event and the time of receipt of the advertising packet.

FIG. 10 is an example flowchart for analyzing the time period between the time of the injection event and the time of receipt of the advertising packet. At step 1002, the time period (item 830) is analyzed to determine whether it is less than a specified threshold. In some embodiments, if a short time (e.g., below the threshold) has elapsed since the injection event, then it is likely that the computing device was near the medication delivery device during the injection event. This may indicate that the advertising packet was correctly received (e.g., validation data 808b) by the computing device. In some embodiments, if a long time (e.g., greater than a threshold) has elapsed since the injection event, then it is likely that the computing device was not near the medication delivery device during the injection event. This may indicate that the advertising packet was erroneously received (e.g., validation data 808*a*) from the medication delivery device a different user. In some embodiments, the threshold may be greater than 2 minutes, 4 minutes, 6 minutes, 8 minutes, 10 minutes, 20 minutes, 40 minutes, or any time within the range of 2 and 40 minutes.

Based on the validation data 808*a* and 808*b*, the computing device determines whether to prompt the user for additional information or ignore the advertising packet 810 or to include the injection event information in the medication log 812. As described herein, if the time period (item 830) is greater than the threshold, then the computing device may determine that the advertising packet was erroneously received (validation data 808*a*) and prompt the user for additional information or ignore the advertising packet 810. Alternatively, if the time period (item 830) is less than the threshold, then the computing device may determine that the advertising packet was correctly received (validation data 808*b*) and include the injection event information in the medication log 812.

In some embodiments, the flowchart depicted in FIG. 10 may also be modified to allow the computing device to choose between not just two courses of action, but three courses of action. For example, if the time period (item 830) is lower than a first threshold, the computing device may determine that the packet was likely to be correctly received and will include the dose event information in the log. If the time of receipt is between the first threshold and a second, higher threshold, the computing device may determine that the packet may have been incorrectly received and will prompt the user for additional information. If the time of receipt is greater than the second threshold, the computing device may determine to ignore the advertising packet.

Figure 11:
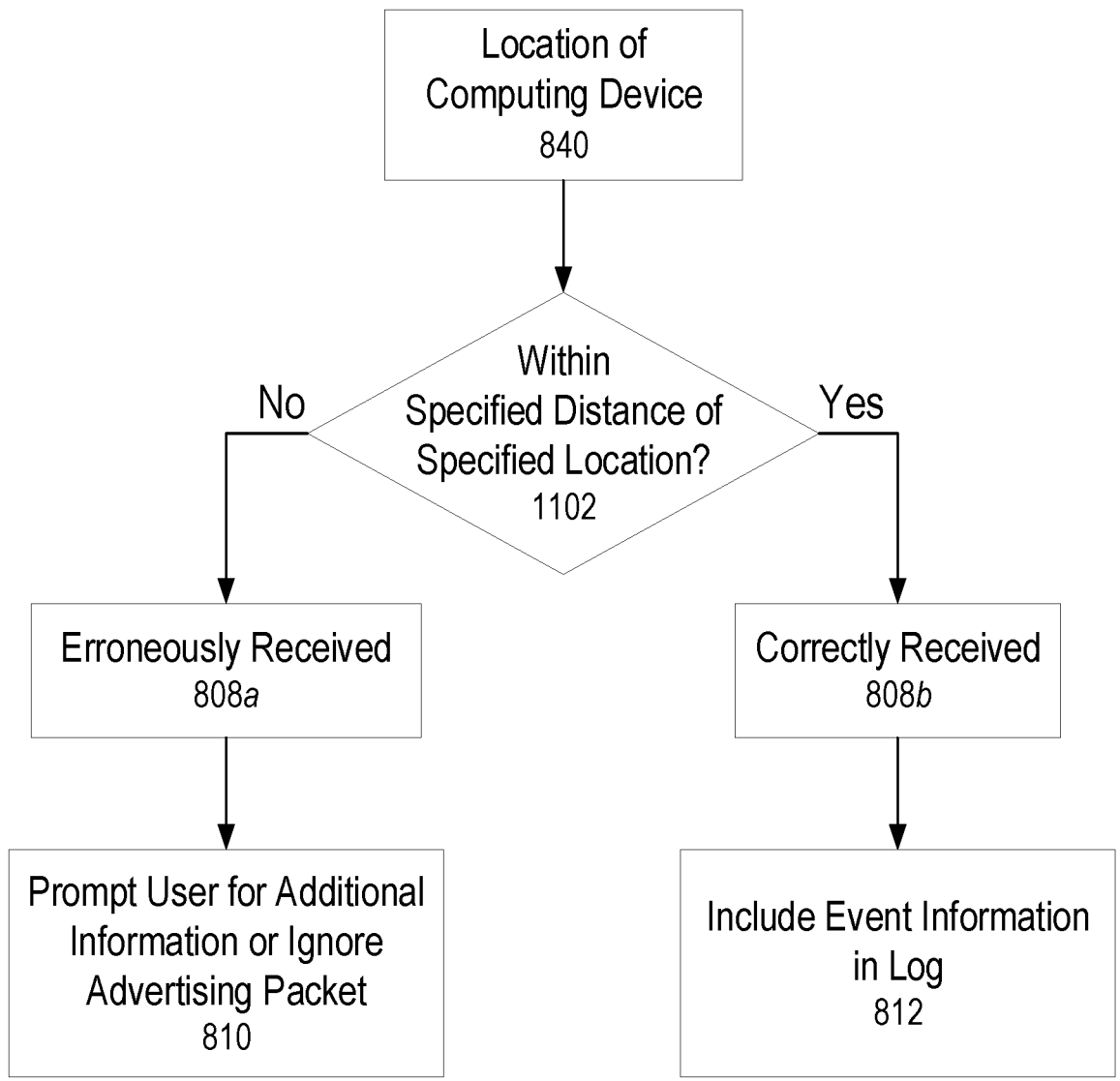
FIG. 11 is an example flowchart for analyzing the location of the computing device at a time of receipt of the advertising packet.

FIG. 11 is an example flowchart for analyzing the location of the computing device at a time of receipt of the advertising packet, according to some embodiments. At step 1102, the location of the computing device (item 840) is analyzed to determine if the computing device is within a specified distance of a specified location. In some embodiments, different locations may be associated with different population and/or housing densities (e.g., the population density of a location in the city is greater than that of a rural neighborhood). If the location of the computing device is associated with a low population density, it may be likely that the advertising packet was correctly received (e.g., validation data 808*b*) by the computing device. Conversely, if the location of the computing device is associated with a high population density, there may be a greater possibility that the advertising packet was erroneously received (e.g., validation data 808*a*) by the computing device.

Additionally or alternatively, in some embodiments, a user may typically take a dose of medication in one or more locations, such as the user's home. If the location of the computing device is close to a typical dosing location(s) (e.g., within the specified distance of a specified location), then it may be likely that the advertising packet was correctly received (validation data 808*b*) by the computing device. If the location of the computing device is not close to a typical dosing location (e.g., not within the specified distance of a specified location), then it may likely that the advertising packet was erroneously received (validation data 808*a*) by the computing device.

According to some embodiments, the specified location and/or the specified distance may be pre-set by a user. For example, the user may indicate (e.g., by interacting with a user interface of the computing device) one or more locations where they may typically take their medication (e.g., using the medication delivery device). Further, they may indicate a distance (e.g., radius) from the location where they expect the computing device to be during the injection event. In some embodiments, the one or more locations and the distance from the one or more locations may be automatically determined by the system. In some embodiments, a machine learning model may be trained based on data about the location of the computing device at the time of past injection events. The trained machine learning model may then be used to determine whether a location of the computing device at the time of receipt of the advertising packing is within range of a typical location for an injection event.

Based on the validation data 808*a* and 808*b*, the computing device determines whether to prompt the user for additional information or ignore the advertising packet 810 or to include the injection event information in the medication log 812. As described herein, if the location of the computing device (item 840) is not within the specified distance of a specified location, then the computing device may determine that the advertising packet was erroneously received (validation data 808*a*) and prompt the user for additional information or ignore the advertising packet 810. Alternatively, if the location of the computing device (item 840) is less than the threshold, then the computing device may determine that the advertising packet was correctly received (validation data 808*b*) and include the injection event information in the medication log 812.

In some embodiments, the flowchart depicted in FIG. 11 may be modified to allow the computing device to choose between not just two courses of action, but three courses of action. For example, if the location of the computing device (item 840) is within a first threshold distance of the specified location(s), the computing device may determine that the packet was likely to be correctly received and will include the dose event information in the log. If the location of the computing device is not within the first threshold distance of the specified location(s) but is within a second (higher) threshold distance of the specified location(s), the computing device may determine that the packet may have been incorrectly received and will prompt the user for additional information. If the location of the computing device is not within the second threshold distance of the specified location(s), the computing device may determine to ignore the advertising packet.

Figure 12:
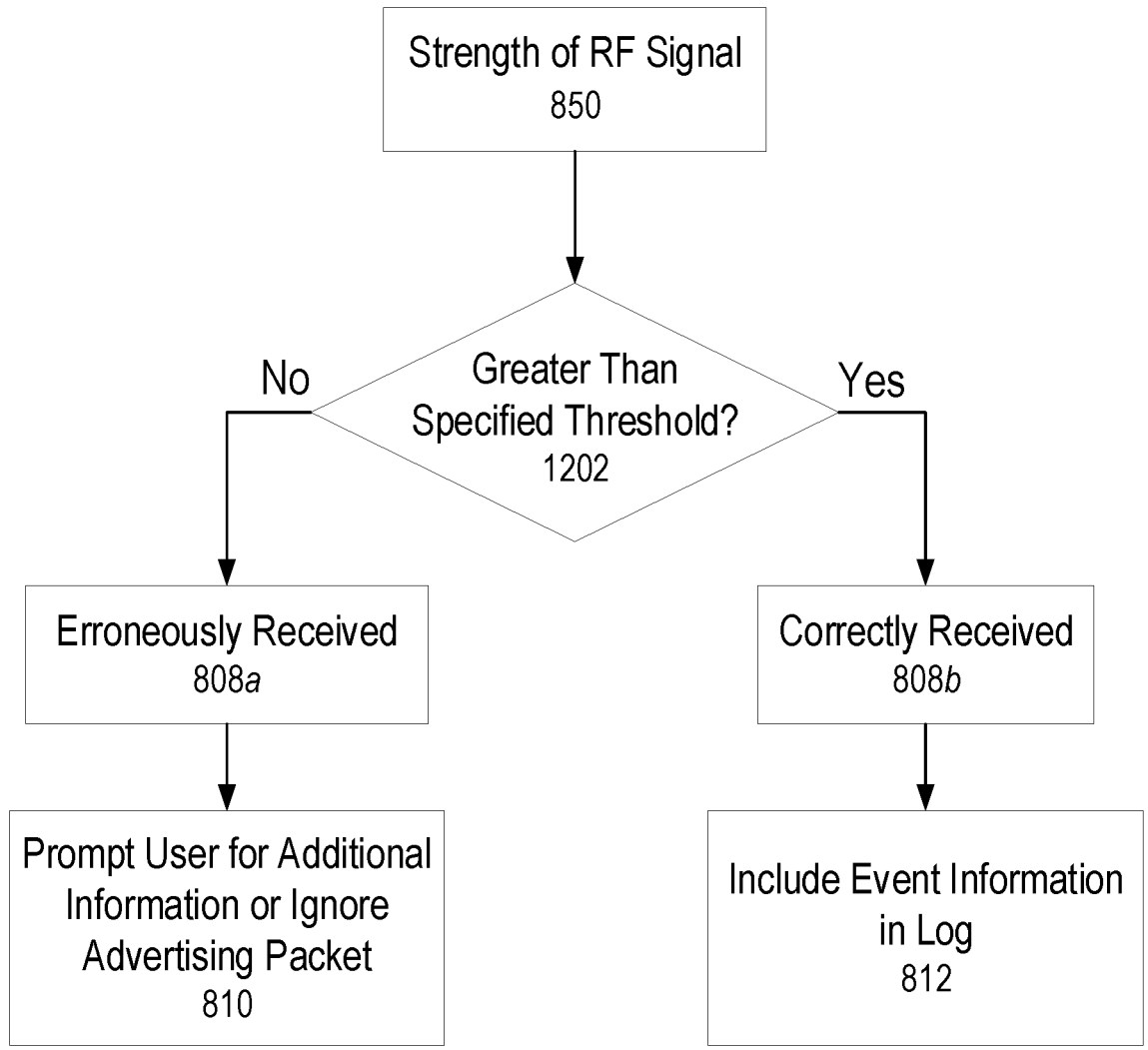
FIG. 12 is an example flowchart for analyzing the strength of the RF signal at a time of receipt of the advertising packet.

FIG. 12 is an example flowchart for analyzing the strength of the RF signal at a time of receipt of the advertising packet, according to some embodiments. At step 1202, the strength of the RF signal is analyzed to determine whether it is greater than a specified threshold. In some embodiments, a high RF signal (e.g., greater than the threshold) may indicate that the medication delivery device is within close proximity to the computing device. This may suggest that it is likely that the advertising packet was correctly received (e.g., validation data 808*b*) by the computing device. If the RF signal is low (e.g., not greater than the threshold), then this may indicate that the medication delivery device is not within close proximity to the computing device, suggesting it is possible that the advertising packet was erroneously received (e.g., validation data 808*a*) by the computing device.

Based on the validation data 808*a* and 808*b*, the computing device determines whether to prompt the user for additional information or ignore the advertising packet 810 or to include the injection event information in the medication log 812. As described herein, if the strength of the RF signal (item 850) is not greater than the specified threshold, then the computing device may determine that the advertising packet was erroneously received (validation data 808*a*) and prompt the user for additional information or ignore the advertising packet 810. Alternatively, if the strength of the RF signal (item 850) is greater than the specified threshold, then the computing device may determine that the advertising packet was correctly received (validation data 808*b*) and include the injection event information in the medication log 812.

In some embodiments, the flowchart depicted in FIG. 12 may be modified to allow the computing device to choose between not just two courses of action, but three courses of action. For example, if the strength of the RF signal (item 850) is greater than a first threshold signal strength, the computing device may determine that the packet was likely to be correctly received and will include the dose event information in the log. If the strength of the RF signal is less than the first threshold signal strength but greater than a second (lower) threshold signal strength, the computing device may determine that the packet may have been incorrectly received and will prompt the user for additional information. If the RF signal strength is less than the second threshold signal strength, the computing device may determine to ignore the advertising packet.

Figure 13:
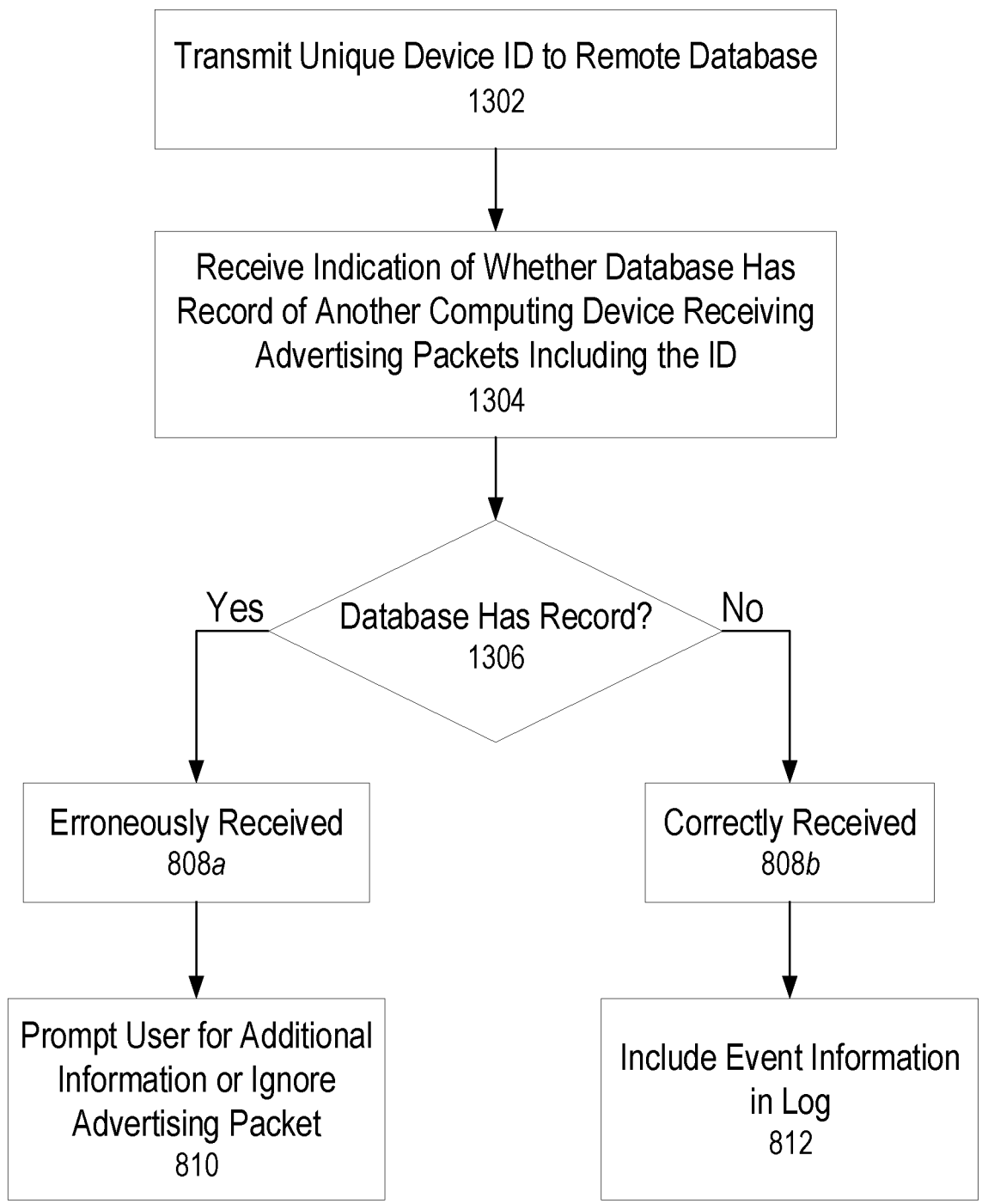
FIG. 13 is an example flowchart for analyzing remote database records indicative of whether another computing device has already received advertising packets from the medication delivery device.

FIG. 13 is an example flowchart for analyzing remote database records indicative of whether another computing device has already received advertising packets from the medication delivery device (item 860), according to some embodiments. At step 1302, the computing device transmits a unique device identifier to a remote database. In some embodiments, the device identifier is unique to the medication delivery device and is included in the advertising packets broadcast by the medication delivery device. Upon receiving the advertising packet, the computing device transmits the unique identifier included in the advertising packet to a remote database. In some embodiments, the remote database may be accessible over a WiFi network, a cellular network, and/or by using any other suitable means for accessing the remote database, as aspects of the technology described herein are not limited in that respect. In some embodiments, the remote database may include data storing information about advertising packets received on other computing devices. For example, the database may indicate that Computer X previously received an advertising packet from a medication delivery device associated with a unique identifier "Y".

At step 1304, the computing device receives, from the remote database, an indication of whether the database has a record of another computing device receiving advertising packets including the unique identifier included in the advertising packet received by the computing device. In some embodiments, at step 1306, if the database has a record of another computing device receiving the packets, then this may suggest that the injection event information has already been captured by another device and it is likely that the advertising packet was erroneously received (e.g., validation data 808*a*) by the computing device. If the database does not have a record of another computing device receiving the advertising packets, then it may be likely that the advertising packet was correctly received (e.g., validation data 808*b*) by the computing device.

Based on the validation data 808*a* and 808*b*, the computing device determines whether to prompt the user for additional information or ignore the advertising packet 810 or to include the injection event information in the medication log 812. As described herein, if the database indicates that another computing device has already received advertising packets including the device ID, then the computing device may determine that the advertising packet was erroneously received (validation data 808*a*) and prompt the user for additional information or ignore the advertising packet 810. Alternatively, if the database indicates that another computing device has not yet received advertising packets including the ID, then the computing device may determine that the advertising packet was correctly received (validation data 808*b*) and include the injection event information in the medication log 812. In some embodiments, the computing device may then update the remote database to indicate that the computing device received advertising packets including the unique identifier.

Figure 14:
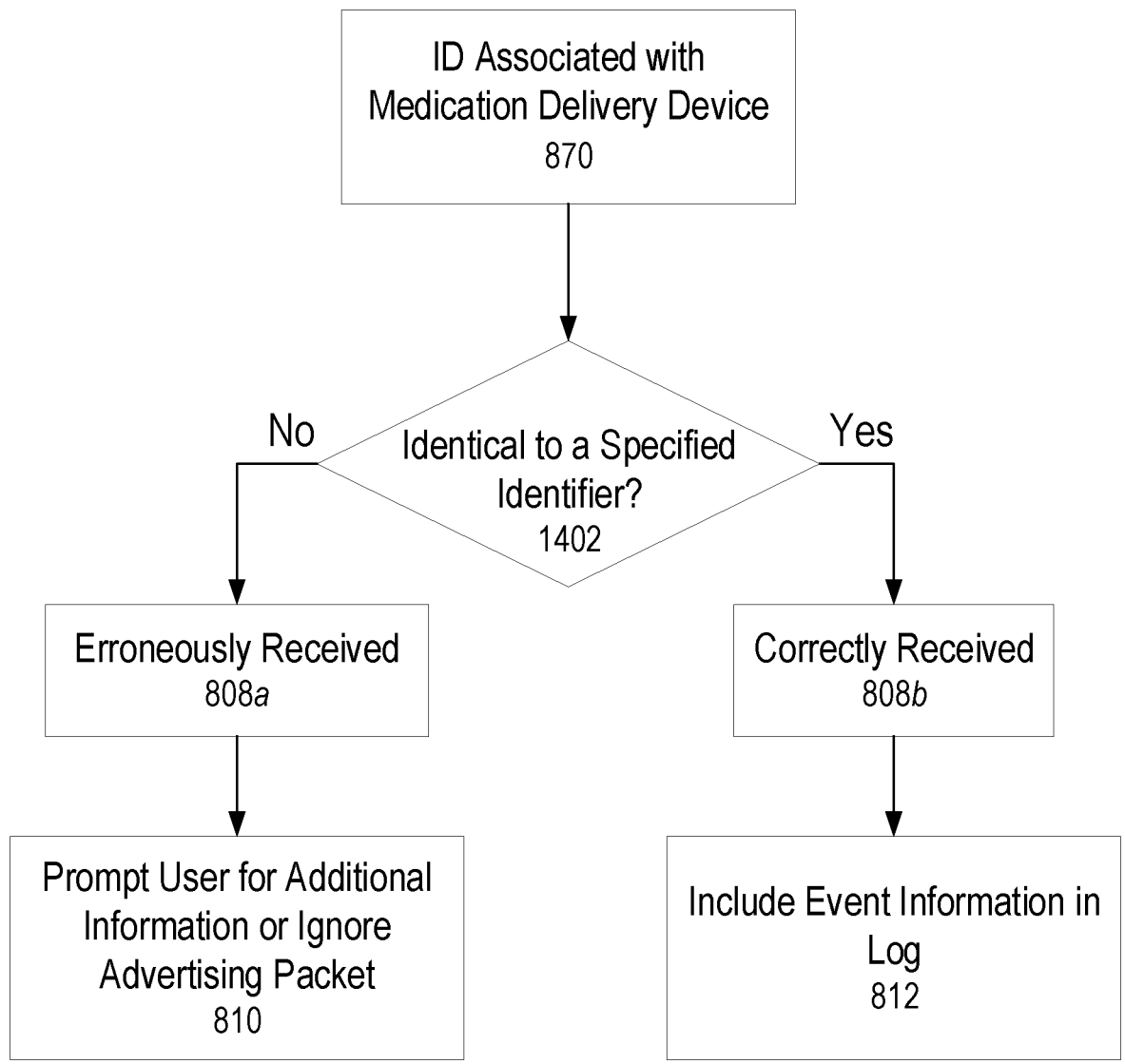
FIG. 14 is an example flowchart for analyzing an identifier associated with the medication delivery device.

FIG. 14 is an example flowchart for analyzing an identifier associated with the medication delivery device, according to some embodiments. At step 1402, the identifier associated with the medication delivery device (item 870) is analyzed to determine whether it is identical to an identifier that was prescribed to the patient (e.g., user of the computing device). In some embodiments, the advertising packet includes an identifier that is unique to the medication delivery device, as described herein including with respect to FIG. 13. In some embodiments, if the device ID included in the advertising packet received by the computing device matches a patient ID assigned or prescribed to a user of the computing device, then this may indicate that the advertising packet was correctly received (e.g., validation data 808*b*) by the computing device. If the device ID does not match the patient ID assigned to the user, then this may indicate that the advertising packet was erroneously received (e.g., validation data 808*a*) by the computing device.

In some embodiments, a patient ID may be stored in a remote database. For example, a doctor may update a remote database to assign the patient ID to the user of the computing device. The patient ID may match a device ID associated with the medication delivery device prescribed to the same user. In some embodiments, the computing device may transmit the device ID included in the advertising packet to the remote database. The computing device may then receive, from the remote database, an indication of whether the device ID matches the patient ID assigned to the user and stored in the database. In some embodiments, the remote database may be accessible over a WiFi network, a cellular network, and/or by using any other suitable means for accessing the remote database, as aspects of the technology described herein are not limited in that respect. In some embodiments, the computing device may then analyze the indication received from the remote database to determine the validation data 808.

Based on the validation data 808*a* and 808*b*, the computing device determines whether to prompt the user for additional information or ignore the advertising packet 810 or to include the injection event information in the medication log 812. As described herein, if the device ID (item 860) is not identical to the specified identifier (e.g., the patient ID), then the computing device may determine that the advertising packet was erroneously received (validation data 808*a*) and prompt the user for additional information or ignore the advertising packet 810. Alternatively, if the device ID (item 806) is identical to the specified ID, then the computing device may determine that the advertising packet was correctly received (validation data 808*b*) and include the injection event information in the medication log 812.

Figure 15:
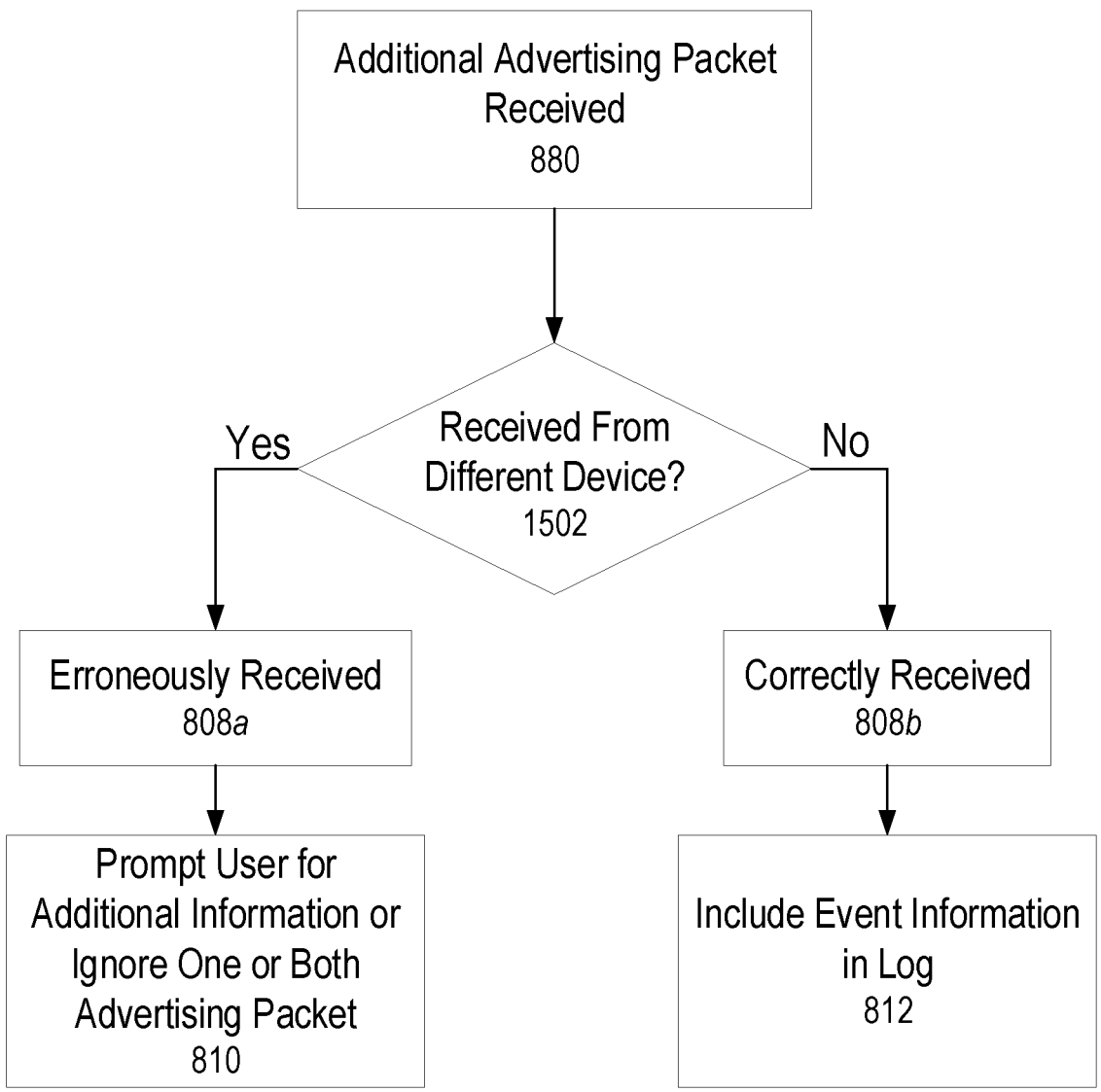
FIG. 15 is an example flowchart for analyzing an additional advertising packet received by the computing device at the same time as the advertising packet.

In some embodiments, the computing device may receive more than one advertising packet at the same time, or within a short time period of each other. For example, the computing device may receive multiple advertising packets within a short time in a public restroom where multiple patients may be taking a dose of medication. FIG. 15 is an example flowchart for analyzing an additional advertising packet (e.g., advertising packet B) received by the computing device at the same time as the advertising packet (e.g., advertising packet A), according to some embodiments. At step 1502, advertising packet B (item 880) may be analyzed to determine whether it was received from a different computing device than advertising packet A. In some embodiments, this may include analyzing an identifier included in advertising packet B and/or other data associated with advertising packet B. If it is determined that advertising packet B was not received from the same computing device as advertising packet A, then this may indicate that one or both advertising packets were erroneously received (e.g., validation data 808*a*) by the computing device. If it is determined that advertising packet B was received from the same computing device as advertising packet A, then this may indicate that both advertising packets were correctly received (e.g., validation data 808*b*) by the computing device.

Based on the validation data 808*a* and 808*b*, the computing device determines whether to prompt the user for additional information or ignore one or both advertising packets 810 or to include the injection event information in the medication log 812. As described herein, if the additional advertising packet (item 880) was not received from the same medication delivery device, then the computing device may determine that the advertising packet was erroneously received (validation data 808*a*) and prompt the user for additional information or ignore one or both advertising packets 810. Alternatively, if the additional advertising packet (item 870) was received from the same medication delivery device, then the computing device may determine that the advertising packet was correctly received (validation data 808*b*) and include the injection event information in the medication log 812.

Figure 16:
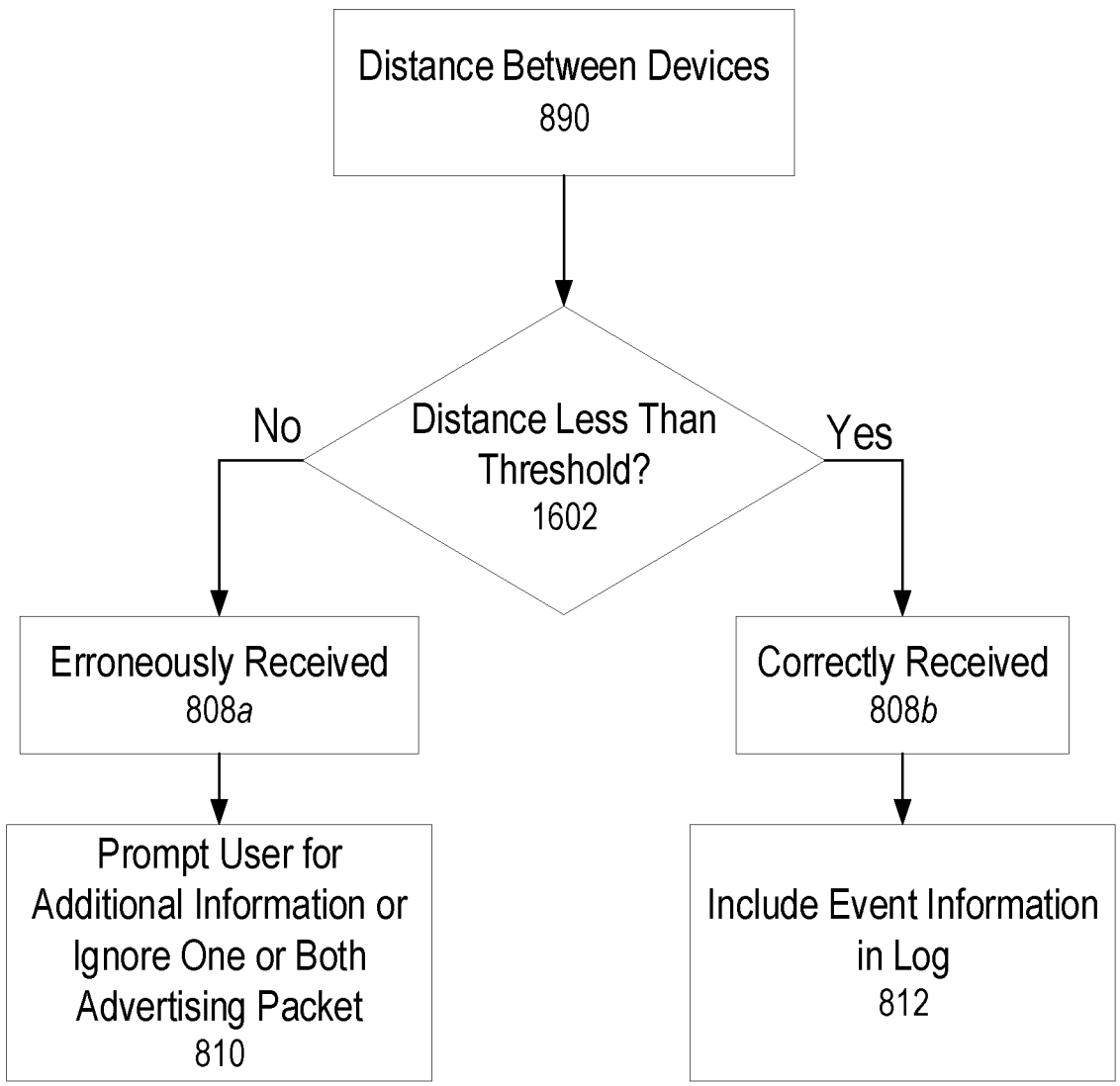
FIG. 16 is an example flowchart for analyzing a distance between the medication delivery device and the computing device.

FIG. 16 is an example flowchart for analyzing the distance between the computing device and the medication delivery device. In some embodiments, determining the distance between the devices may include determining the amount of time that it takes the advertising packet to travel between the two devices. In some embodiments, the time of travel may additionally or alternatively be included as contextual data (e.g., contextual data 806). The distance between the two devices may be calculated based on the time of travel and the speed of light through air. Such techniques can be used with various protocols. As an example, this technique may be applied when processing packets according to UWB, which may enable a relatively accurate calculation of distance based on the travel time of the advertising packet.

At step 1602, the distance between the medication delivery device and the computing device is analyzed to determine whether it is less than the specified threshold. In some embodiments, a short distance (e.g., lower than the threshold) may indicate that the medication delivery device is within close proximity to the computing device. This may suggest that it is likely that the advertising packet was correctly received (e.g., validation data 808*b*) by the computing device. If the distance is far (e.g., greater than the threshold), then this may indicate that the medication delivery device is not within close proximity to the computing device, suggesting that it is possible that the advertising packet was erroneously received (e.g., validation data 808*a*) by the computing device.

Based on the validation data 808*a* and 808*b*, the computing device determines whether to prompt the user for additional information or ignore the advertising packet 810 or to include the injection event information in the medication log 812. As described herein, if the distance between the devices (item 890) is not less than the specified threshold, then the computing device may determine that the advertising packet was erroneously received (validation data 808*a*) and prompt the user for additional information or ignore the advertising packet 810. Alternatively, if the distance between the devices (item 890) is less than the specified threshold, then the computing device may determine that the advertising packet was correctly received (validation data 808*b*) and include the injection event information in the medication log 812.

In some embodiments, the flowchart depicted in FIG. 16 may be modified to allow the computing device to choose between not just two courses of action, but three courses of action. For example, if the distance between the devices (item 890) is less than a first threshold distance, the computing device may determine that the packet was likely to be correctly received and will include the dose event information in the log. If the distance between the devices is greater than the first threshold distance but less than a second (greater) threshold distance, the computing device may determine that the packet may have been incorrectly received and will prompt the user for additional information. If the distance between the devices is greater than the second threshold distance, the computing device may determine to ignore the advertising packet.

The various methods or processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above.

The terms "program," "software," and/or "application" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in non-transitory computer-readable storage media in any suitable form. Data structures may have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more methods, of which examples have been provided. The acts performed as part of a method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This allows elements to optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

Various aspects are described in this disclosure, which include, but are not limited to, the following aspects:

1. A computerized method, comprising: receiving, from a wireless communication interface of a medication delivery device, an advertising packet comprising injection event information associated with an injection event generated by the medication delivery device, wherein the medication delivery device comprises (a) a reservoir configured to hold medication, (b) an actuating button for initiating an injection of the medication, and (c) a processing circuit in communication with the wireless communication interface; analyzing contextual data associated with the advertising packet to determine validation data; and choosing, based on the validation data, between implementing any two or three of the following actions: (i) include the injection event information in a medication log, (ii) prompt a user for additional information regarding the advertising packet, or (iii) ignore the advertising packet.

2. The computerized method of claim 1, wherein receiving the advertising packet comprises receiving a Bluetooth Low Energy (BLE) advertising packet.

3. The computerized method of any of claims 1-2, wherein the medication delivery device further comprises: one or more skin contact sensors to detect skin contact; and an accelerometer configured to output a signal representative of a sensed acceleration.

4. The computerized method of claim 1, wherein analyzing the contextual data associated with the advertising packet comprises analyzing data associated with a time of receipt of the advertising packet.

The computerized method of claim 4, wherein choosing between implementing any two or three of the actions comprises: determining whether a time of the injection event is within a specified range of at least one specified time; and upon determining that the time of the injection event is within the specified range of the at least one specified time, including the injection event information in the medication log.

6. The computerized method of claim 5, wherein the at least one specified time is automatically determined based on past injection times associated with the user.
7. The computerized method of claim 1, wherein analyzing the contextual data associated with the advertising packet comprises analyzing data associated with a time period between a time of the injection event and a time of receipt of the advertising packet.
8. The computerized method of claim 7, wherein choosing between implementing any two or three of the actions comprises: determining whether the time period between the time of the injection event and the time of receipt of the advertising packet is less than a threshold; and upon determining that the time period between the time of the injection event and the time of receipt of the advertising packet is less than the threshold, including the injection event information in the medication log.
9. The computerized method of claim 1, wherein analyzing the contextual data associated with the advertising packet comprises analyzing data associated with a location of a computing device that received the advertising packet.
10. The computerized method of claim 9, wherein choosing between implementing any two or three of the actions comprises: determining whether the location is within a specified distance of at least one specified location; and upon determining that the location is within the specified distance of the at least one specified location, including the injection event information in the medication log.
11. The computerized method of claim 10, wherein the at least one specified location is automatically determined based on past injection locations associated with the user.
12. The computerized method of claim 1, wherein analyzing the contextual data associated with the advertising packet comprises analyzing data associated with a strength of a radio frequency (RF) signal associated with the advertising packet.
13. The computerized method of claim 12, wherein choosing between implementing any two or three of the actions comprises: comparing the strength of the RF signal to a specified threshold; and upon determining that the strength of the RF signal exceeds the specified threshold, including the injection event information in the medication log.
14. The computerized method of claim 1, wherein analyzing the contextual data associated with the advertising packet comprises analyzing data associated with a distance between the medication delivery device and a computing device that received the advertising packet.
15. The computerized method of claim 14, wherein choosing between implementing any two or three of the actions comprises: comparing the distance to a specified threshold; and upon determining that the distance is less than the specified threshold, including the injection event information in the medication log.
16. The computerized method of claim 1, wherein the advertising packet includes a unique medication delivery device identifier, and wherein analyzing the contextual data associated with the advertising packet comprises: transmitting the unique medication delivery device identifier to a remote database; and receiving, in response to the transmission, an indication of whether the remote database has a record of another computing device receiving advertising packets including the unique medication delivery device identifier.
17. The computerized method of claim 16, wherein choosing between implementing any two or three of the actions comprises: determining, based on the received indication, whether the remote database has the record of another computing device receiving advertising packets including the unique medication delivery device identifier; and upon determining that the remote database does not have the record, including the injection event information in the medication log.
18. The computerized method of claim 1, wherein analyzing the contextual data associated with the advertising packet comprises analyzing data indicative of an identifier associated with the medication delivery device.
19. The computerized method of claim 18, wherein choosing between implementing any two or three of the actions comprises: determining whether the identifier associated with the medication delivery device is identical to a specified identifier uniquely associated and prescribed to an expected user of the medication delivery device by a health care provider; and upon determining that the identifier is identical to the specified identifier, including the injection event information in the medication log.
20. The computerized method of claim 1, wherein analyzing the contextual data associated with the advertising packet comprises analyzing data related to an additional advertising packet received by the at least one processor.
21. The computerized method of claim 20, wherein choosing between implementing any two or three of the actions comprises: determining whether the additional advertising packet was received from a second medication delivery device that is different from the medication delivery device; and upon determining that the additional advertising packet was not received from the second medication delivery device, including the injection event information in the medication log.
22. The computerized method of claim 1, wherein analyzing the contextual data associated with the advertising packet comprises analyzing two or more of (a) data associated with a time of receipt of the advertising packet, (b) data associated with a time period between a time of the injection event and a time of receipt of the advertising packet, (c) data associated with a location of a computing device that received the advertising packet, (d) data associated with a strength of a radio frequency (RF) signal associated with the advertising packet, (e) data associated with a distance between the medication delivery device and the computing device, (f) data indicative of whether a remote database has a record of another computing device receiving advertising packets including a unique medication delivery device identifier, (g) data indicative of an identifier associated with the medication delivery device, and (h) data related to an additional advertising packet.
23. The computerized method of claim 1-22, further comprising issuing a scan response after receiving the advertising packet.
24. The computerized method of claim 1-23, wherein the scan response is configured to cause the medication delivery device to turn off.
25. The computerized method of any of claims 1-24, wherein prompting the user for the additional information comprises prompting the user to confirm whether the injection event information should be included in the medication log.

26. The computerized method of any of claims 1-25, wherein determining whether to (i) include the injection event information in the medication log, (ii) prompt the user for the additional information, or (iii) ignore the advertising packet consists essentially of choosing between implementing only two of (i), (ii), and (iii).

27. The computerized method of any of claim 1-26, wherein the injection event information comprises a date and/or time of the injection event.

28. A non-transitory computer-readable media comprising instructions that, when executed by one or more processors on a computing device, are operable to cause the one or more processors to execute the method of any of claims 1-27.

29. A system comprising a memory storing instructions, and a processor configured to execute the instructions to perform the method of any of claims 1-27.

What is claimed is:

1. A computerized method, comprising:
    receiving, from a wireless communication interface of a medication delivery device, an advertising packet comprising injection event information associated with an injection event generated by the medication delivery device, wherein the medication delivery device comprises (a) a reservoir configured to hold medication, (b) an actuating button for initiating an injection of the medication, and (c) a processing circuit in communication with the wireless communication interface;
    analyzing data associated with a time of receipt of the advertising packet to determine validation data; and
    choosing, based on the validation data, between: (i) including or not including the injection event information in a medication log without prompting a user and (ii) prompting the user to confirm whether to include said injection event information in said medication log;
    wherein said choosing comprises:
        determining whether the time of receipt is within a specified range of at least one specified time of day at which the user is expected to take the medication, and upon determining that the time of receipt is within the specified range of the at least one specified time of day, including the injection event information in the medication log without prompting the user.

2. The computerized method of claim 1, wherein receiving the advertising packet comprises receiving a Bluetooth Low Energy (BLE) advertising packet.

3. The computerized method of claim 1, wherein the medication delivery device further comprises:
    one or more skin contact sensors to detect skin contact; and
    an accelerometer configured to output a signal representative of a sensed acceleration.

4. The computerized method of claim 1, wherein the at least one specified time of day is automatically determined based on past injection times associated with the user.

5. The computerized method of claim 1, wherein the validation data comprises data indicative of
    a location of a computing device that received the advertising packet.

6. The computerized method of claim 5, wherein the choosing comprises:
    determining whether the location is within a specified distance of at least one specified location; and
    upon determining that the location is within the specified distance of the at least one specified location, including the injection event information in the medication log without prompting the user.

7. The computerized method of claim 6, wherein the at least one specified location is automatically determined based on past injection locations associated with the user.

8. The computerized method of claim 1, wherein the advertising packet further comprises a unique medication delivery device identifier, the method further comprising:
    transmitting the unique medication delivery device identifier to a remote database; and
    receiving, in response to the transmission, an indication of whether the remote database has a record of another computing device receiving advertising packets including the unique medication delivery device identifier;
    wherein the choosing is based at least in part on the received indication.

9. The computerized method of claim 8, wherein the choosing comprises:
    determining, based on the received indication, whether the remote database has the record of another computing device receiving advertising packets including the unique medication delivery device identifier; and
    upon determining that the remote database does not have the record, including the injection event information in the medication log without prompting the user.

10. The computerized method of claim 1, further comprising issuing a scan response after receiving the advertising packet.

11. The computerized method of claim 10, wherein the scan response is configured to cause the medication delivery device to turn off.

12. The computerized method of claim 1, wherein the injection event information comprises a date and/or time of the injection event.

* * * * *